(12) United States Patent
Siddiqi

(10) Patent No.: US 9,415,399 B2
(45) Date of Patent: Aug. 16, 2016

(54) DEVICE FOR MIXING AND SEPARATION OF MAGNETIC PARTICLES

(71) Applicant: Sigris Research, Inc., Brea, CA (US)

(72) Inventor: Iqbal W. Siddiqi, Brea, CA (US)

(73) Assignee: Sigris Research, Inc., Brea, CA (US)

( * ) Notice: Subject to any disclaimer, the term of this patent is extended or adjusted under 35 U.S.C. 154(b) by 350 days.

(21) Appl. No.: 14/047,888

(22) Filed: Oct. 7, 2013

(65) Prior Publication Data

US 2014/0251887 A1 Sep. 11, 2014

Related U.S. Application Data

(60) Continuation-in-part of application No. 13/725,950, filed on Dec. 21, 2012, now abandoned, which is a continuation of application No. 13/299,290, filed on Nov. 17, 2011, now Pat. No. 8,361,316, which is a continuation of application No. 12/387,158, filed on Apr. 29, 2009, now Pat. No. 8,088,285, which is a division of application No. 11/079,695, filed on Mar. 15, 2005, now Pat. No. 7,632,405, which is a division of application No. 10/290,514, filed on Nov. 8, 2002, now Pat. No. 6,884,357, which is a continuation-in-part of application No. 09/771,665, filed on Jan. 30, 2001, now Pat. No. 6,500,343, which is a continuation-in-part of application No. 09/476,258, filed on Jan. 3, 2000, now Pat. No. 6,228,268, which is a continuation-in-part of application No. 09/476,260, filed on Jan. 3, 2000, now Pat. No. 6,231,760, which is a division of application No. 08/902,164, filed on Jul. 29, 1997, now Pat. No. 6,033,574.

(51) Int. Cl.

| | |
|---|---|
| *B03C 1/12* | (2006.01) |
| *B03C 1/14* | (2006.01) |
| *B03C 1/24* | (2006.01) |
| *B03C 1/28* | (2006.01) |
| *B03C 1/01* | (2006.01) |
| *B01F 13/10* | (2006.01) |
| *B01F 13/08* | (2006.01) |
| *B01L 9/00* | (2006.01) |
| *G01N 35/00* | (2006.01) |

(52) U.S. Cl.
CPC ............... *B03C 1/12* (2013.01); *B01F 13/0809* (2013.01); *B01F 13/1013* (2013.01); *B01F 13/1022* (2013.01); *B03C 1/01* (2013.01); *B03C 1/14* (2013.01); *B03C 1/24* (2013.01); *B03C 1/288* (2013.01); *B01L 9/523* (2013.01); *G01N 35/0098* (2013.01); *Y10T 436/25* (2015.01); *Y10T 436/25375* (2015.01)

(58) Field of Classification Search
CPC ............ B03C 1/12; B03C 1/14; B03C 1/288; B03C 1/24; B03C 1/01; B01F 13/1022; B01F 13/1013; B01F 13/0809; G01N 35/0098; Y10T 436/25; Y10T 436/25375
See application file for complete search history.

(56) References Cited

U.S. PATENT DOCUMENTS

| | | | | |
|---|---|---|---|---|
| 6,033,574 A | * | 3/2000 | Siddiqi | ..................... B03C 1/01 210/695 |
| 6,231,760 B1 | * | 5/2001 | Siddiqi | ..................... B03C 1/01 210/222 |

(Continued)

*Primary Examiner* — David A Reifsnyder
(74) *Attorney, Agent, or Firm* — Knobbe, Martens Olson & Bear, LLP

(57) ABSTRACT

An apparatus for mixing and separating magnetic particles in a liquid comprises a holder having a plurality of apertures configured as an array of rows and columns and a plurality of containers capable of receiving liquid containing magnetic particles, each container being sized to be placed in one of the apertures; plural magnets capable of being moved relative to the containers between a first position and a second position to change the position of the magnets and magnetic particles in the container; and a drive mechanism for moving the magnets between positions at a sufficiently high speed that the particles do not settle down due to gravitational forces during motion between the first and second positions.

17 Claims, 19 Drawing Sheets

(56) References Cited

U.S. PATENT DOCUMENTS

| | | | |
|---|---|---|---|
| 6,500,343 B2 * | 12/2002 | Siddiqi | B03C 1/01 210/695 |
| 6,884,357 B2 * | 4/2005 | Siddiqi | B01F 13/0809 210/695 |
| 7,632,405 B2 * | 12/2009 | Siddiqi | B01F 13/0809 209/217 |

* cited by examiner

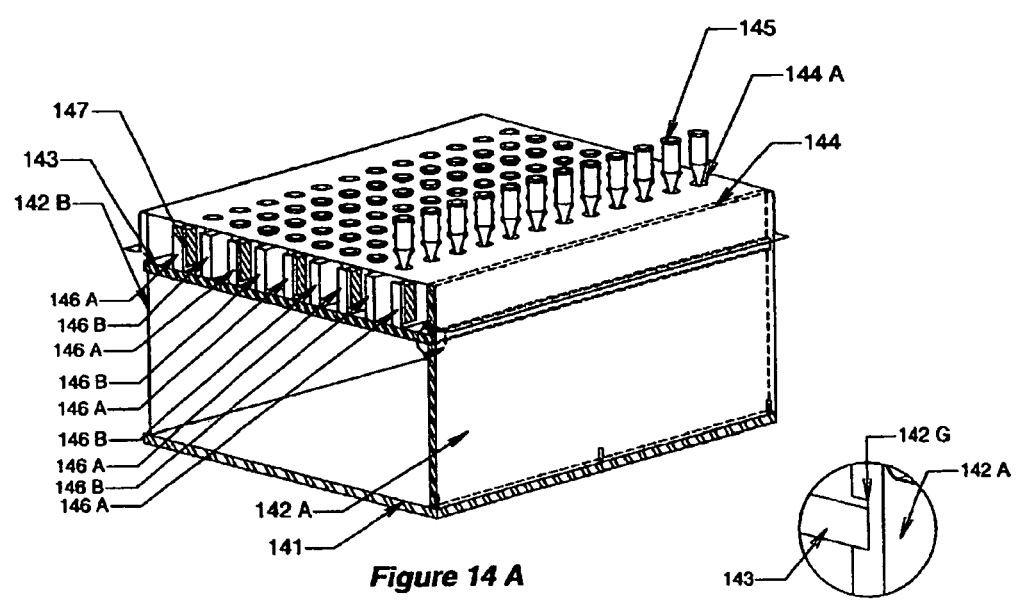
*Figure 14 A*
*Figure 14 B*
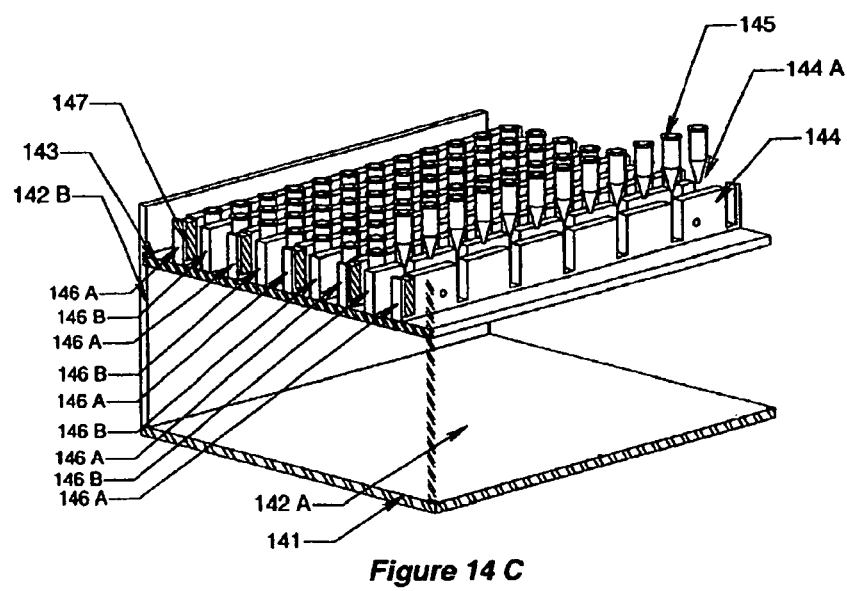
*Figure 14 C*

DEVICE FOR MIXING AND SEPARATION OF MAGNETIC PARTICLES

CROSS-REFERENCE TO RELATED APPLICATIONS

This application is a division of application Ser. No. 11/079,695, filed Mar. 15, 2005, now abandoned, which is a division of application Ser. No. 10/290,514, filed Nov. 8, 2002, now U.S. Pat. No. 6,884,357, which is a continuation-in-part of application Ser. No. 09/771,665, filed on Jan. 30, 2001, now U.S. Pat. No. 6,500,343, which is continuation-in-part of application Ser. No. 09/476,258, filed on Jan. 3, 2000, now U.S. Pat. No. 6,228,268, and a continuation-in-part of application Ser. No. 09/476,260, filed on Jan. 3, 2000, now U.S. Pat. No. 6,231,760, which is a division of application Ser. No. 08/902,164, filed Jul. 29, 1997, now U.S. Pat. No. 6,033,574.

BACKGROUND OF THE INVENTION

1. Field of the Invention

The present invention relates to an apparatus and a method for mixing and separation of magnetic particles for the purpose of isolating substances from a nonmagnetic liquid test medium.

2. Description of Related Art

Magnetic separation of biomolecules and cells based on magnetic particles and employing biospecific affinity reactions is advantageous in terms of selectivity, simplicity, and speed. The technique has proved to be quite useful in analytical and preparative biotechnology and is now being increasingly used for bioassays and isolation of target substances such as cells, proteins, nucleic acid sequences and the like.

As used herein, the term "receptor" refers to any substance or group of substances having biospecific binding affinity for a given ligand, to the substantial exclusion of other substances. Among the receptors susceptible to biospecific binding affinity reactions are antibodies (both monoclonal and polyclonol), antibody fragments, enzymes, nucleic acids, lectins and the like. The term "ligand" refers to substances such as antigens, haptens, and various cell associated structures having at least one characteristic determinant or epitope, which substances are capable of being biospecifically recognized by and bound to a receptor. The term "target substance" refers to either member of a biospecific binding affinity pair, i.e., a pair of substances or a substance and a structure exhibiting a mutual affinity of interaction, and includes such things as biological cells or cell components, biospecific ligands, and receptors.

Affinity separation refers to known process techniques where a target substance mixed with other substances in a liquid medium is bound to the surface of a solid phase by a biospecific affinity binding reaction. Substances, which lack the specific molecule or structure of the target substance, are not bound to the solid phase and can be removed to effect the separation of the bound substance or vice versa. Small particles, particularly polymeric spherical particles as solid phase, have proved to be quite useful, as they can be conveniently coated with biomolecules, provide a very high surface area, and give reasonable reaction kinetics. Separations of the particles containing bound target substance (bound material) from the liquid medium (free material) may be accomplished by filtration or gravitational effects, e.g., settling, or by centrifugation.

Separation of bound/free fractions is greatly simplified by employing magnetizable particles, which allows the particle bound substance to be separated by applying a magnetic field. Small magnetizable particles are well known in the art, as is their use in the separations involving immunological and other biospecific affinity reactions. Small magnetizable particles generally fall into two broad categories. The first category includes particles that are permanently magnetized, and the second comprises particles that become magnetic only when subjected to a magnetic field. The latter are referred to as paramagnetic or superparamagnetic particles and are usually preferred over the permanently magnetized particles.

For many applications, the surface of paramagnetic particles is coated with a suitable ligand or receptor, such as antibodies, lectins, oligo nucleotides, or other bioreactive molecules, which can selectively bind a target substance in a mixture with other substances. Examples of small magnetic particles or beads are disclosed in U.S. Pat. Nos. 4,230,685, 4,554,088, and 4,628,037. The use of paramagnetic particles is taught in publications, "Application of Magnetic Beads in Bioassays," by B., Haukanes, and C. Kvam, Bio/Technology, 11:60-63 (1993); "Removal of Neuroblastoma Cells from Bone Marrow with Monoclonal Antibodies Conjugated to Magnetic Microspheres" by J. G. Treleaven et al. Lancet, Jan. 14, 1984, pages 70-73; "Depletion of T Lymphocytes from Human Bone Marrow," by F. Vartdal et. al. Transplantation, 43: 366-71 (1987); "Magnetic Monosized Polymer Particles for Fast and Specific Fractionation of Human Mononuclear Cells," by T. Lea et. al., Scandinavian Journal of Immunology, 22: 207-16 (1985); and "Advances in Biomagnetic Separations," (1994), M. Uhlen et. al. eds. Eaton Publishing Co., Natick, Mass.

The magnetic separation process typically involves mixing the sample with paramagnetic particles in a liquid medium to bind the target substance by affinity reaction, and then separating the bound particle/target complex from the sample medium by applying a magnetic field. All magnetic particles except those particles that are colloidal, settle in time. The liquid medium, therefore, must be agitated to some degree to keep the particles suspended for a sufficient period of time to allow the bioaffinity binding reaction to occur. Examples of known agitation methods include shaking, swirling, rocking, rotation, or similar manipulations of a partially filled container. In some cases the affinity bond between the target substance and the paramagnetic particles is relatively weak so as to be disrupted by strong turbulence in the liquid medium. In other cases biological target substances such as cells, cellular fractions, and enzyme complexes are extremely fragile and will likewise be disrupted or denatured by excess turbulence.

Excess turbulence is just one of several significant drawbacks and deficiencies of apparatus and methods used in the prior art for biomagnetic separations. The specific configuration of a magnetic separation apparatus used for separating particle-bound target complex from the liquid medium will depend on the nature and size of magnetic particles. Paramagnetic particles in the size range of 0.1 to 300 µm are readily removed by means of commercially available magnetic separation devices. Examples of such magnetic separation devices are the Dynal MPC series of separators manufactured by Dynal, Inc., Lake Success, N.Y.; and BioMag Separator series devices manufactured by PerSeptive Diagnostics, Cambridge, Mass.; and a magnetic separator rack described in U.S. Pat. No. 4,895,650. These devices employ permanent magnets located externally to a container holding a test medium and provide only for separation. Mixing of the paramagnetic particles in the test medium for affinity binding reaction must be done separately. For example, Dynal MPC series of separators requires a separate mixing apparatus, a Dynal Sample Mixer, for agitating the test media. The process must be actively monitored through various stages of mixing, washing, and separation, and requires significant intervention from the operator. Accordingly, the efficiency of these devices is necessarily limited by the skill and effectiveness of the operator.

U.S. Pat. No. 4,910,148 describes a device and method for separating cancer cells from healthy cells. Immunoreactive paramagnetic particles and bone marrow cells are mixed by agitating the liquid medium on a rocking platform. Once the particles have bound to the cancer cells, they are separated from the liquid medium by magnets located externally on the platform. Although such mixing minimizes the liquid turbulence, it does not provide an efficient degree of contact between the particles and the target substance. Moreover, the utility of this device is limited to the separation of cells from relatively large sample volumes.

U.S. Pat. No. 5,238,812 describes a complicated device for rapid mixing to enhance bioaffinity binding reactions employing a U-tube-like structure as mixer. The U-tube is rapidly rocked or rotated for 5 to 15 seconds to mix the magnetic particles in the test medium, and then a magnet is brought in close proximity to the bottom of the U-tube to separate the magnetic particles. As stated in the '812 patent, its utility is limited to treating very small volumes (<1000 μl) of test medium.

U.S. Pat. No. 5,336,760 describes a mixing and magnetic separation device comprising a chamber attached to a platform with one or more magnets located close to the container and an intricate mechanism of gears and motor to rotate the platform. Immuno-reactive paramagnetic particles are mixed in the test medium by first placing a stainless steel "keeper" between the chamber and the magnet to shield it from the magnetic field. Then the platform is rotated between vertical and horizontal positions. The particles in the test medium are mixed by end-over-end movement of the chamber. Following the mixing, the "keeper" is removed so that the magnetic particles are captured by the exposed magnetic field. Besides requiring a complicated mechanism, agitation of the liquid medium by end-over-end rotation does not mix relatively buoyant particles efficiently, and the liquid turbulence will tend to shear off or damage the target substance.

U.S. Pat. No. 5,110,624, relates to a method of preparing magnetizable porous particles and describes a flow-through magnetically stabilized fluidized bed (MSFB) column to isolate proteins from cell lysate. The MSFB column is loosely packed with a bed of magnetizable particles and equipped with means of creating a stationary magnetic field that runs parallel to the flow of solution through the column. The particles are maintained in a magnetically stabilized fluidized bed by adjusting the rate of flow of the solution and the strength of the magnetic field. This is a complicated technique requiring precise adjustment of the flow rate and magnetic strength so that the combined effect of fluid velocity and magnetic attraction exactly counterbalances the effect of gravity on the particles. Moreover, the design of MSFB is not optimized for use with small test volumes, and cannot be made optimal for applications such as bioassays or cell separations.

International patent application WO 91/09308 published Jun. 27, 1991 discloses a separating and resuspending process and apparatus. This application teaches that rotation of a magnet around the container containing paramagnetic particles induces the particles to remain as a compact aggregate (in close proximity to the magnet source) and roll over one another. The application teaches that this method fails to produce resuspension of the particles. The application WO 91/09308, discloses that the magnetic particles must be subjected to sequential magnetic fields situated opposite each other in order to effect resuspension. The application describes a device comprising a chamber located between two electromagnets, which are energized and de-energized to aggregate the magnetic particles alternately at the two magnets. The application teaches that alternately energizing and de-energizing the two electromagnets at a sufficiently rapid rate keeps the particles suspended in the center of the chamber. This method limits movement of the particles to a relatively small distance, significantly reducing the collision frequency between particles and the target substance, necessary for affinity binding which is a major reason for mixing the paramagnetic particles in the liquid medium. Moreover, a significant fraction of the particles, particularly particle-cell complexes may escape the magnetic field by gravitational settling to the bottom of chamber and will be lost during aspiration of the liquid medium following the aggregation step.

Japanese patent No. JP58193687 entitled Agitation And Separation Of Microscopic Material is directed to separation of microorganisms by mixing magnetized ultra-fine magnetic wire with microorganisms containing magnetic particles. The mixing is accomplished by a rotary magnetic field, which also acts to separate the microorganisms after a mixing step. This patent is concerned with separation of microorganisms that contain internally ultra-fine magnetic particles. Such microorganisms are well known in the art, a particular example being magneto spirillium, a bacteria known to synthesize ultra fine magnetic particles. Such microorganisms would not and cannot be used as magnetic particles for mixing and separation of a target species as envisioned by the present invention. The Japanese patent's requirement for linearly-connected ultra-fine magnetic particles refers to a wire which is most likely used to create a high gradient magnetic field (HGMF) to collect or precipitate the magnetite-containing bacteria over the surface of these wires. Such a technique has no application to the process of affinity separation of a target substance from a liquid test medium as envisioned by the present invention since it relies on the magnetic properties of the micro-organisms (the target substance itself) to effect a reaction.

The applicable known procedures have shortcomings, including the requirement for separate mechanically complex mixing mechanisms, as well as various process constraints and inefficiencies. The present invention provides devices and methods for magnetic mixing and separation which are of relatively simple construction and operation, which can be adapted to process large or small volumes of test liquid, and which can process multiple test samples simultaneously. Additionally, the invention provides a single device for both mixing and separation and a method which maximizes the mixing efficiency of the paramagnetic particles in the liquid medium without causing detrimental liquid turbulence, using an angular acceleration of at least 0.84 radians/second/second (hereinafter referred as rads/s$^2$).

SUMMARY OF THE INVENTION

According to the present invention, the affinity separation of a target substance from a liquid test medium is carried out by mixing magnetic particles bearing surface immobilized ligands or receptors to promote specific affinity binding reaction between the magnetic particles and the target substance. The liquid test medium with the magnetic particles in a suitable container is removably mounted in the apparatus of the present invention. In one preferred embodiment, a single magnetic field gradient is created in the liquid test medium. This gradient induces the magnetic particles to move towards the inside wall of the container nearest to the magnetic source. Relative movement between the magnetic source and the aggregating magnetic particles is started using a preferred angular acceleration of about 1.05 to about 4.19 rads/s$^2$ to mix the magnetic particles in the test medium and is continued for a sufficient time to ensure optimum binding of the target substance by affinity reaction. In addition, concurrently with the relative movement, the magnetic source may be moved from one end of the container to the other thereby effectively scanning along the length of the container by the magnetic field gradient. When the relative movement between the magnet and the magnetic particles is stopped, the magnetic particles are immobilized as a relatively compact aggregate on the inside wall of the container nearest to the magnetic source. The test medium may then be removed while the magnetic particles are retained on the wall of the container and may be subjected to further processing, as desired.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings, wherein:

FIG. 13 B shows a view corresponding to FIG. 13A without the rotor plate and showing concentrically arranged magnets in a staggered pattern and the containers positioned in from of each magnet.

FIG. 13 C shows an exploded view corresponding to FIG. 1A, and showing various components of the embodiment.

FIG. 14 B shows the partially cut away view corresponding to FIG. 14 A and showing the details of the linear sliding mechanism of a groove in the side plate and the moveable support plate.

FIG. 14 C shows a view corresponding to FIG. 14 A without the container holding plate and showing linear arrays of staggered magnets and the corresponding containers.

FIG. 14 D shows a partial top view corresponding to FIG. 14 A showing the positions of magnets in the three rows of magnet arrays and the corresponding position of the containers.

FIG. 15 A shows an exploded view corresponding to FIG. 15 and showing different parts of the device and their respective positions.

FIG. 15 B shows a side view corresponding to FIG. 15 A illustrating the relative positions of magnets on the two support structures.

FIG. 15 C shows a top view corresponding to FIG. 15 with the positions of the magnets between the wells of the 96-well microplate brought in by the vertical motion of one support structure.

FIG. 15 D shows a top view corresponding to FIG. 15 with the positions of the magnets between the wells of the 96-well microplate brought in by the vertical motion of second support structure.

FIG. 16 B shows a side view, corresponding to FIG. 16 A and shows the positions of the container and the two magnets mounted on the two rotors which upon rotation alternately positions the magnets on the opposite sides of the container.

DETAILED DESCRIPTION OF THE PREFERRED EMBODIMENTS

Figure 1:
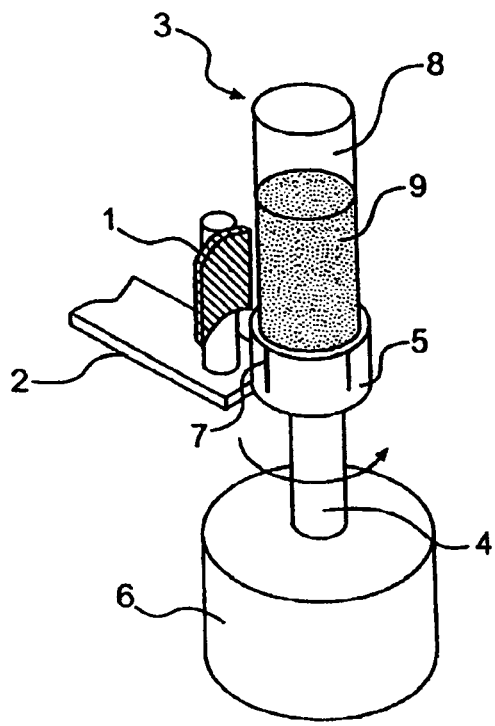
FIG. 1 shows a perspective view of a preferred embodiment of the invention, which includes a stationary magnet placed next to a mobile container partially filled with a liquid test medium containing magnetic particles.

The following description is provided to enable any person skilled in the art to make and use the invention and sets forth the best modes contemplated by the inventor for carrying out his invention. Various modifications, however, will remain readily apparent to those skilled in the art, since the principles of the present invention are defined herein specifically to provide an apparatus and method for mixing and separating samples containing paramagnetic particles, which maximize the mixing efficiency of the particles without causing significant liquid medium turbulence.

The invention permits rapid, efficient, and clean separation of a target substance from test media and is particularly useful in the affinity magnetic separations of organic, biochemical, or cellular components of interest from, for example, assay reaction mixtures, cell cultures, body fluids and the like. The invention includes a novel mixing system wherein the magnetic particles are mixed within a relatively motionless test liquid by magnetic means disposed external to the container holding the test liquid. The invention also includes an apparatus and method wherein magnetic particles while mixing and confined in a magnetic zone are concurrently linearly displaced to scan large volumes of test medium for affinity separation with a small concentration of magnetic particles. The invention provides an apparatus in which both the processes of mixing and separation are carried out by a common magnetic means disposed in a single apparatus, thereby making it simpler and more practical to use.

The apparatus of the invention comprises at least one container for holding a test medium, external magnetic means to generate a magnetic field gradient within the test medium, and means for creating a magnetically induced movement of the magnetic particles within the test medium. The apparatus of the invention may also include a linear motion mechanism to move the magnetic means for scanning large volume of the liquid test medium. The container for performing the described mixing and separation is preferably of cylindrical configuration, made of a nonmagnetic material such as glass or plastic. Preferably, the container has at least one opening for receiving the test medium containing the magnetic particles.

The magnetic means may comprise one or more permanent or electromagnets disposed externally to the container for generating magnetic field gradients within the liquid test medium. In a preferred embodiment, the magnet is a permanent magnet of a rare earth alloy such as anisotropic sintered materials composed of neodymium-iron-boron or samarium-cobalt. The magnet is disposed external to the container so as to define a magnetic field gradient cavity in a desired cross-section of the test medium. The tam cavity is employed because the magnetic field gradient acts to confine or concentrate the magnetic particles much as if they were enclosed within a cavity. The magnetic field strength in the cavity is normally stronger at a part of the internal surface of the container closer to the magnet (locus of magnetic force) than it is elsewhere in the cavity and becomes negligible outside the cavity. As a result, magnetic particles in the test medium near this locus are subject to considerably greater magnetic force than those farther from it and tend to aggregate as a relatively compact mass on the inner surface of the lateral wall of the container closest to magnetic means. As the particles are all clustered in the vicinity of the magnetic means, they also tend to stick to each other by non-magnetic forces of compression and surface tension. The degree of compression in the aggregated particles depends on the field strength of magnetic means and is particularly relevant in the case of particles with diameters of a few microns, such as are usually employed in affinity separation. Such compacted particles can remain aggregated even after the removal of the magnetic field and usually require vigorous shaking of the test medium to re-disperse. A carefully balanced magnetic field strength in the test medium will pull the particles out of suspension into an aggregate, but will not be so strong as to overly compress the aggregate. According to the present invention, a desired magnetic field strength within the magnetic field cavity of the test medium may be created by appropriately adjusting the distance between the magnet and the container. The apparatus of the invention provides means for adjusting the distance between a magnet and the container.

In certain preferred embodiments, two magnets may be located on the opposite sides of the container, preferably with similar magnetic poles facing each other, to distort the magnetic flux lines and generate two magnetic field gradients and two loci of magnetic force forming in one cavity. Such an arrangement is particularly useful for agitating magnetic particles, as described below. In a particularly advantageous arrangement, an assembly comprising a vertical array of magnets is positioned exterior to the container to create multiple magnetic field gradient cavities within desired cross-sections of the test medium.

The present invention provides two methods for agitating and mixing the magnetic particles within the test medium while maintaining the test medium substantially motionless with respect to the container. Both methods are based on changing the relative angular position between magnetic means and the aggregated particles on the inside surface of the container at an angular acceleration of at least $0.84$ rad/s$^2$ and preferably between about $1.05$ to $4.19$ rads/s$^2$. The first method comprises rotating the container with respect to a stationary magnet. The magnetic field gradient cavity defined by the magnet in this instance is hence stationary. At an angular acceleration of about $0.83$ to about $4.19$ rads/s$^2$, the test medium is not agitated and rotates with the container. The second method comprises rotating a magnet about a stationary container. The magnetic field gradient cavity defined by the magnet in this instance is rotating. It may be noted that using either method causes a change in the angular position between the aggregated particles within the container and the magnet.

As the relative angular position between the container and the magnet is displaced at an angular acceleration of at least $0.84$ rad/s$^2$ and preferably between about $1.05$ to about $4.19$ rad/s$^2$, the aggregated mass of particles move with the wall of the container to a position of weaker magnetic field. At this position, the stronger magnetic field in the vicinity of the magnetic means begins to pull off the particles from the aggregated mass, the trajectories of the particles being pulled off depends on the angular position of the aggregated mass and magnet. As the particles are pulled, they move and form chains of particles, due to the induced magnetic dipole on the particles by the applied magnetic field. As the chains accelerate towards the magnet, fluid drag force causes them to break creating a cloud of magnetic particles in the fluid medium. At a constant angular acceleration of either the container or magnet, the relative angular position between the magnet and the internal surface of the container bearing the aggregated particles recedes continuously and causes the particles to move ceaselessly in angular trajectories within the test medium thereby enabling the re-suspension and mixing of magnetic particles. The parameter, angular acceleration, is important in the mixing of the magnetic particles as described in the present invention. Applicant has found that at angular accelerations below 0.84 rad/s$^2$, the aggregated mass of particles on the inside wall of the container do not move sufficiently rapidly to overcome the strong magnetic field in the vicinity of the magnetic means, resulting in a rolling mass of aggregated particles. Angular acceleration between about 1.05 to 4.19 rad/s$^2$ permits the aggregated mass of particles to move away with the wall of the container to a position of weaker magnetic field thereby effecting mixing as described above.

As regards particles it should be noted that the force pulling a magnetic particle through a fluid medium is the product of its magnetic saturation and field gradient and the viscous force opposing particle motion, which is governed by Stokes Law. The displacement of particle trajectories in a continuous manner is based on the action of magnetomotive force acting at a continuously changing angle between the magnet and the paramagnetic particles which results in a mixing process without fluid turbulence. Furthermore, this mixing process significantly increases the collision frequency between the particles and target species thereby enhancing the efficiency of the affinity binding reaction.

A suitable angular acceleration can be calculated on the basis of radius of the container, forces of gravity, buoyancy, fluid friction and magnetic field strength. However, for a given set of parameters, the intensity of the magnetic field or fields and the appropriate angular acceleration will be modulated experimentally. It should be noted that too high acceleration will not allow the particles sufficient time to detach from the aggregated mass and particles will be spread over the circumference of the inner wall of the container. Similarly, too slow acceleration such as about 0.10 to 0.21 rads/s$^2$ will produce a rolling mass of the aggregated particles. In both cases, re-suspension and mixing of the particles will be prevented. The field strength in the magnetic field cavity of the test medium must also be balanced so as to allow the aggregated particles to move with the wall of the container. It will be appreciated that a fixed magnet position is inconvenient when the desired particle size may vary considerably. In such situations, it is advantageous to be able to adjust the distance between the magnet and the container to create the optimum field strength in the magnetic field cavity of the fluid medium.

Although angular acceleration in the sense described above can be obtained by continuous rotation and provides satisfactory mixing of magnetic particles, in certain situations it is advantageous to provide a step-wise change of a predetermined angular position. For example, the relative angular position may be changed to 90 or 180 degrees in a single step at a significantly higher angular acceleration than is useful in continuous rotation method. Such steps may be repeated more than once, provided a suitable time delay is imposed between such steps. Applicant has found that angular acceleration as high as 300 rads/s$^2$ may applied when the relative angular position is changed to 180° in a single step mode provided a time delay of at least 0.5 second is imposed between subsequent steps. Such repeated step-wise change of a predetermined angular position provides a very efficient mixing of magnetic particles. It should be noted that the selection of suitable angular acceleration is particularly important in the present invention with respect to the said mixing operation. In general, a specific angular acceleration, to ensure re-suspension and mixing, will depend on the size, density and magnetic susceptibility of the particles, the cross sectional diameter of the container, the density and viscosity of the fluid test medium and the strength of the magnetic field. Although a theoretical calculation of such an angular acceleration is possible, for a given set of parameters an appropriate angular acceleration will be determined experimentally. The International patent application WO 91/09308 cited earlier, discloses that rotating the magnet around the container fails to produce resuspension as the particles remain aggregated. The cited WO 91/09308 is silent on the importance of angular acceleration with regard to resuspending and mixing process of the aggregated particles. As shown in example 1 (see later), Applicant has experimentally verified this teaching of the cited WO 91/09308 and has found that at an angular acceleration at or below 0.21 rads/s$^2$ the particles roll over one another and remain substantially aggregated. As a consequence the affinity binding reaction between particles and target species would be seriously hindered and the isolation efficiency would be reduced to almost zero. The experiments described in Example 2 clearly demonstrate the effect of angular acceleration on the purification efficiency. Applicant has found that angular acceleration above 0.84 rad/s$^2$ and preferably between about 1.05 to 4.19 rad/s$^2$ is necessary to provide useful mixing and resuspension of magnetic particles required in affinity binding reaction for the isolation of a desired target species. By recognizing the importance of angular acceleration the present application overcomes the problem of non-mixing disclosed in the prior art cited above.

Figure 11B:
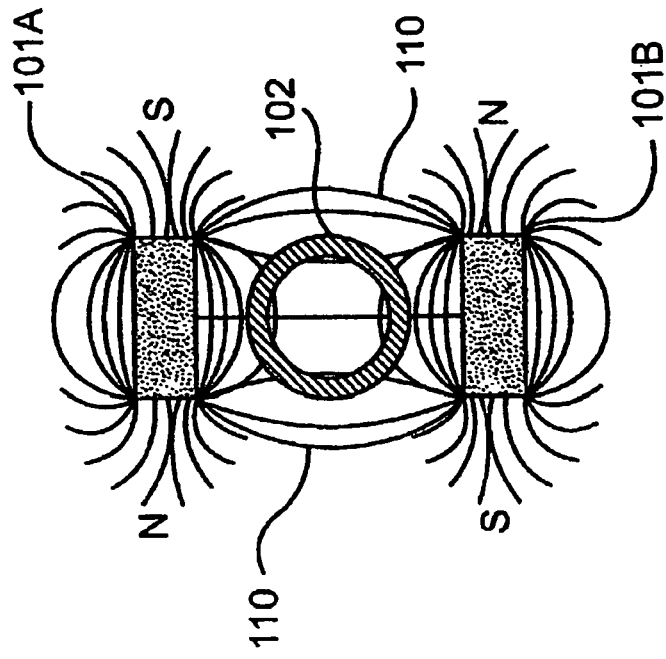
FIGS. 11a and 11b schematically illustrate the magnetic field lines created in a container by two magnets placed on opposite sides of the container.
Figure 11A:
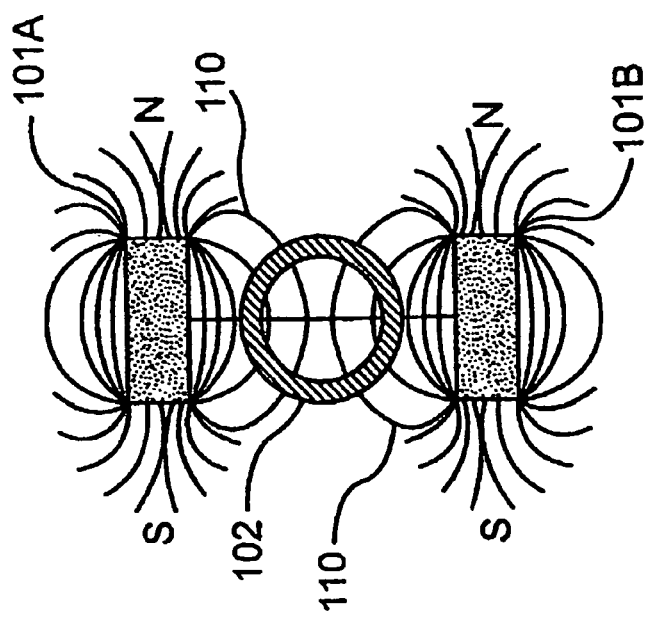

In certain situations, re-suspension and mixing of magnetic particles may be improved by creating a magnetic field gradient in which the magnetic flux lines are distorted by providing two magnets placed on the opposite sides of the container with similar magnetic poles facing each other as shown in FIG. 11a. The magnetic field lines generated by the two magnets are mutually repulsive and the cavity is characterized by having two zones with corresponding loci of high magnetic attraction and a small region in the center (neutral zone) where there is virtually no magnetic field. Since this neutral zone is very small, the random motion of magnetic particles caused by Brownian, gravitational, thermal, and like causes will tend to push most of the magnetic particles into either of the two magnetic field cavities. In a dynamic situation where the relative angular position between the magnet and the container is continuously changing, opposing magnetic flux lines cause the magnetic particles to disperse and mix more efficiently than in the case of a single magnet. However, when two magnets are of opposite poles, as shown in FIG. 11b, the magnetic field lines are mutually attractive and the cavity is characterized by having two relatively small magnetic fields with corresponding loci of high magnetic attractions and a large region in the center (neutral zone) where there is virtually no magnetic field. Such an arrangement may be of use in certain situations.

The separation of magnetic particles from the liquid test medium in accordance with the invention is effected by stopping the rotation of either the magnet or the container to terminate the agitation of the magnetic particles. In the stationary position between magnet and aggregated particles, the magnetic particles within the magnetic field gradient in the fluid medium are attracted to and immobilized at the inside wall of the container nearest to the magnet.

The need for a reliable and readily automated method for resuspending and mixing the aggregated magnetic particles without causing fluid turbulence has not been satisfactorily addressed. Applicant's invention utilizes a new principle of mixing which has allowed, for the first time, integration of a simplified mixing and separation process into a single device.

The present invention provides many advantages over the prior art devices for affinity magnetic separation. The mixing of the present invention provides a high rate of contact between the affinity surface of the magnetic particles and the target substance, thereby enhancing the affinity bonding, without causing fluid turbulence. As a consequence, the hydrodynamic shear forces remain low and will not affect the affinity bond between particle and target substance complex or prevent denaturation, or other damage to the target substance. The process of the present invention can be used for sample volumes as little as 100 µL and can be scaled up to process sample volumes in excess of 100 mL. The present invention is particularly useful for the isolation of human rare cells required in various cell therapies as it permits a level of operating efficiency, which has not been achievable before this.

The purity and yield of the target substance obtained by a particular affinity magnetic separation is largely determined by the mixing process employed to promote the affinity binding reaction between the target substance and the surface of the magnetic particles. The binding reactions require a close contact between the affinity surface and the target substance. The rate of the reaction largely depends on the collision frequency between the two entities and the rate of surface renewal of the magnetic particles. The surface renewal is the process of removing the thin layer of media at the affinity surface and exchanging it with fresh media from the bulk. The hydrodynamic shear force at the affinity surface, therefore, must be carefully balanced so that it is sufficient to remove the thin layer of media without disrupting the affinity bonds. This has been difficult to achieve by past mixing methods based on agitating the fluid medium. The present invention, however, provides a high collision frequency and a substantially balanced shear force by magnetically inducing a controlled movement of the magnetic particles in an essentially motionless fluid medium.

In affinity magnetic separation, the particle concentration is, typically, much greater than the target substance to enhance the yield of the target substance. This is particularly important in the isolation of rare cell types such as mammalian hemopoietic cells where a particle to cell ratio of 20:1 may be required to obtain a desired isolation efficiency. In such applications, magnetic beads of uniform size distribution are required. The high cost of these beads are widely appreciated. The ability to isolate highly purified stem cells may serve in the treatment of lymphomas and leukemias as well as other neoplastic conditions. However, for the isolation of human stem cells, processing of large sample volumes is required. Such a process consumes large quantities of magnetic beads. Thus there is a need to reduce the concentration of magnetic beads without sacrificing the required high purity and yield. One embodiment of the present invention is capable of treating large sample volumes by relatively small concentrations of paramagnetic particles by combining a vertically moving magnet along the length of the container while the container is rotating.

The mixing and separation process of the present invention have particular utility in various laboratory and clinical procedures involving biospecific affinity binding reactions for separations. In such procedures, magnetic particles are used which have their surface coated with one member of a specific affinity binding pair, i.e. ligand or receptor, capable of specifically binding a substance of interest in the test medium.

Such biospecific affinity binding reactions may be employed for the determination or isolation of a wide range of target substances in biological samples. Examples of target substances are, cells, cell components, cell subpopulations (both eukaryotic and prokaryotic), bacteria, viruses, parasites, antigens, specific antibodies, nucleic acid sequences and the like. The apparatus and method of the invention may be used to carry out immunospecific cell separations for the analysis or isolation of cells including, by way of example: tumor cells from bone marrow; T-lymphocytes from peripheral blood or bone marrow; lymphocyte subsets, such as CD2, CD4, CD8, and CD34 from peripheral blood, monocytes; granulocytes and other cell types. The removal or depletion of various cell types may be carried out in a similar manner. The invention may be also be used in the separation or analysis of various bacteria or parasites from food products, culture media, body fluids and the like. Similarly, the apparatus and method of the present invention may be used in: bioassays including immunoassays and nucleic acid probe assays; isolation and detection of DNA and mRNA directly from crude cell lysate; and isolation and detection of proteins.

The magnetic particles preferred for the practice of the invention are noncolloidal paramagnetic or superparamagnetic particles. Such magnetic particles are typically of polymeric material containing a small amount of ferro-magnetic substance such as iron-based oxides, e.g., magnetite, transition metals, or rare earth elements, which causes them to be captured by a magnetic field. The paramagnetic particles useful for practicing the invention should provide for an adequate binding surface capacity for the adsorption or covalent coupling of one member of a specific affinity binding pair, i.e. ligand or receptor. The preferred diameter of a particle is typically in the range between 0.1 to 15 µm. Suitable paramagnetic particles are commercially available from Dynal Inc. of Lake Success, N.Y.; PerSeptive Diagnostics, Inc., of Cambridge, Mass.; and Cortex Biochem Inc., of San Leandro, Calif. Particularly preferred particles are spherical and of uniform size between about 1 and 5 µm in diameter, and contain magnetizable material evenly dispersed throughout. Such particles may be obtained from Dynal under the identification numbers M-280 and M-450 by Dynal Inc. These beads are coated with a thin shell of polystyrene, which provides a defined surface for the immobilization of various ligands or receptors. Such immobilization may be carried out by any one of many well-known techniques; techniques employing either physical adsorption or covalent coupling chemistry are preferred.

Depending on the radius of container, size of magnetic particle and its ferromagnetic content, and other experimental parameters, a suitable magnetic field gradient may be estimated by the magnetic circuit analysis method well known in the magnet art. Appropriate magnetic field gradients may be generated by one or more permanent magnet(s) or electromagnet(s). Permanent magnets are generally preferred for use in laboratory-scale operations and for automated devices employed in clinical diagnostics. A permanent magnet assembly may include soft iron pieces to enhance or modify the magnetic flux lines over a given area inside the container. In some situations, a magnet assembly comprising two soft iron pieces separately attached to north and south poles of the magnet provide a more thorough and uniform mixing. However, larger scale devices or automated devices such as those employed in pharmaceutical or industrial production can be more advantageously produced using electromagnets, since the field gradients can be more easily altered under automatic control to affect various processing steps.

Permanent magnets for practicing the invention preferably have a surface field strength sufficient to attract a majority of the magnetic particles. Permanent magnets of rare earth alloys having a surface field strength in the range of several hundred Gauss to several kilo-Gauss are preferred. High energy permanent magnets made from Neodymium-Iron-Boron or Samarium-Cobalt magnets and characterized by BHmax (maximum energy product) in the range of about 25 to 50 MGOe (megaGauss Oersted) are particularly preferred. Such magnets may be obtained from international Magnaproducts Inc., of Valparaiso, Ind., and many other commercial sources. Preferably the permanent magnets have a rectangular cross-section and may be glued or fixed by mechanical means to a nonmagnetic holding support to form a permanent magnet assembly. The assembly may include a ferromagnetic harness to house the magnet or magnets and to intensify and focus the magnetic field. The magnets are preferably oriented with their magnetic lines of force perpendicular to the vertical axis of the container. Alternate cross-sectional shapes, orientations, and magnetic pole orientation with respect to the container are also envisioned.

Figure 12:
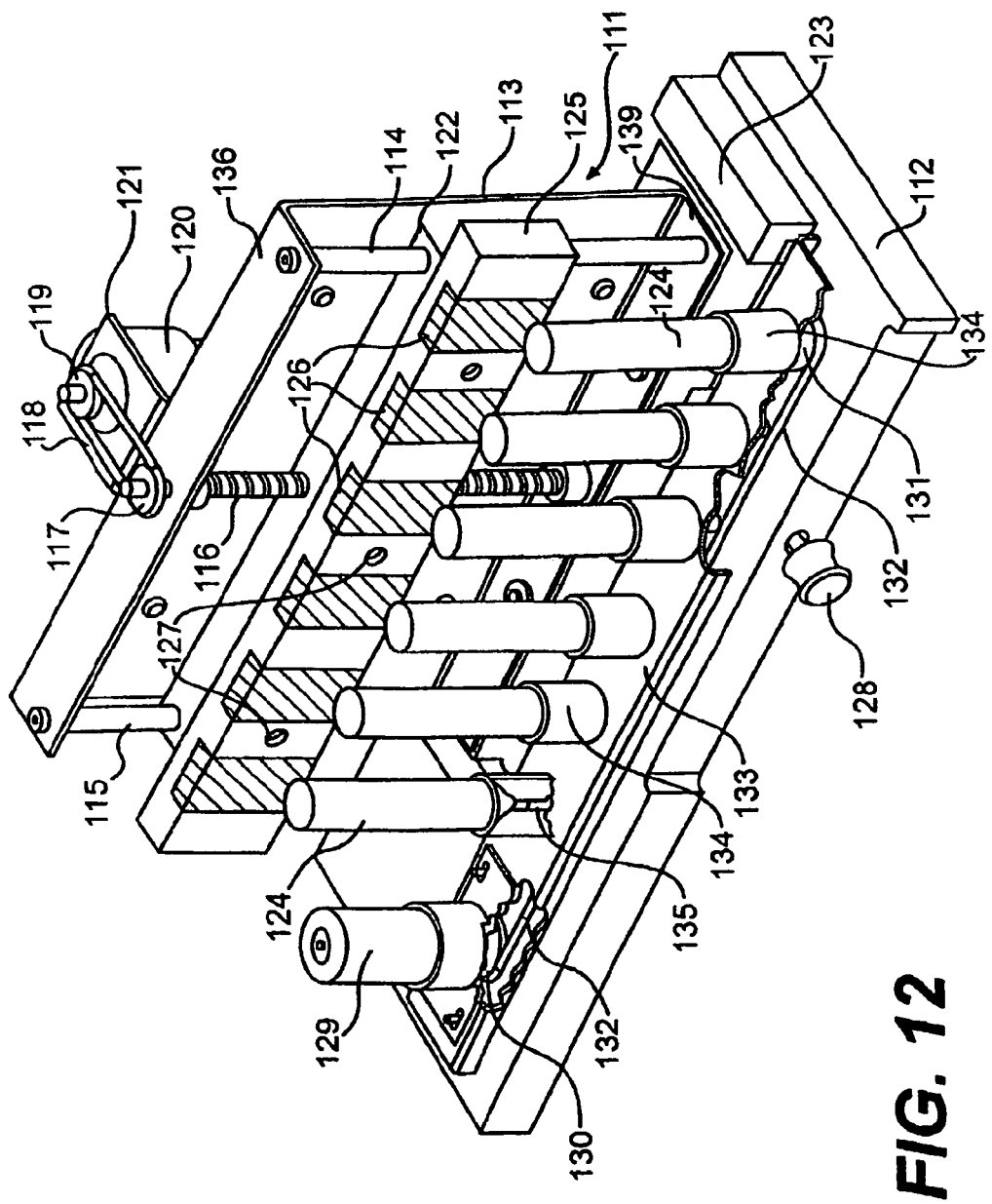
FIG. 12 shows a perspective view of yet another alternate preferred embodiment of the invention which includes a row of magnets mounted on a vertically mobile assembly moveable by a linear drive mechanism and which can be positioned by a sliding mechanism at a desired distance from the corresponding rotatable containers, which are rotated by a common mechanism.

Generally the permanent magnet assembly is placed in close proximity to the container without the magnet extending to the bottom of the container. The distance between each magnet and the container shown in FIGS. 1 through 6 and 12 is adjustable between about 1 mm to about 20 mm to create a desired magnetic field strength within the magnetic field cavity of the test medium. The apparatus shown in these figures includes a means for adjusting the distance between each magnet assembly and the container. An adjusting means is shown in FIG. 12. Lateral (or horizontal) movement of magnets is provided by a linear motion mechanism. Linear motion mechanisms are well known in the art. A simple linear motion mechanism comprises a slider with a rectangular notch or groove, riding on rail with corresponding rectangular shape. Such linear motion mechanisms exist in common furniture drawers. Multiple rails can be provided, as well as ball bearings and rollers if desired. A gear rack and pinion mechanism comprising of a rectangular gear teeth bar (rack) and a mating gear teeth pulley is advantageous when accuracy in the distance between magnet assembly and the container is desired. Suitable gear racks and pinions are available from Designatronics Inc., 2101 Jericho Turnpike, New Hyde Park, N.Y. 11042-5416. Lateral movement of magnet assembly can also be changed by attaching it to an electromagnetic actuator or plunger and such lateral movement may be synchronized with the rotary motion of the container or magnet assembly. Electromagnetic actuators or plungers are also well known in motion control art. While FIG. 12 shows six cylindrical containers, obviously the number can be increased, or decreased to one FIG. 12 further shows vertical movements of magnets driven by screw 116. Obviously structures shown in FIG. 1 and FIG. 4 can be moved by FIG. 12 mechanisms. For instance, the stationary containers of FIGS. 2 and 3 or the stationary magnet of FIG. 1 could be made movable using a screw mechanism, or similar mechanical means, like the one shown in FIG. 12. The magnet position can also be changed by fastening the magnet assembly at a desired position by various male and female fasteners.

Depending on the size and magnetic susceptibility of the particles and the field strength of the magnets and cross-section diameter of the container, the appropriate distance will be determined experimentally. The field strength created in the magnet field cavities should be carefully balanced so that it is sufficient to pull the particles out of suspension, aggregate the particles on the side of the container, and allow the aggregated particles to move with the wall of the container. However, the magnet may be moved closer to the container, as discussed, to increase the field strength in order to separate the particles from the liquid test medium. In certain situations involving the processing of a plurality of containers, it may be advantageous to place the permanent magnet assembly between containers or between rows of containers so that one single permanent magnet assembly can be used to generate a magnetic field cavity in the two containers in its vicinity.

Specifically, in order to move the stationary magnet along the vertical axis of the moving container, as shown in FIG. 1, the solid support 2 may be mechanically fastened to a carriage on a linear slide mechanism similar to the one (122) shown in FIG. 12. The apparatus and method shown in FIG. 1 is simply a one-container variation of FIG. 12.

Figure 2:
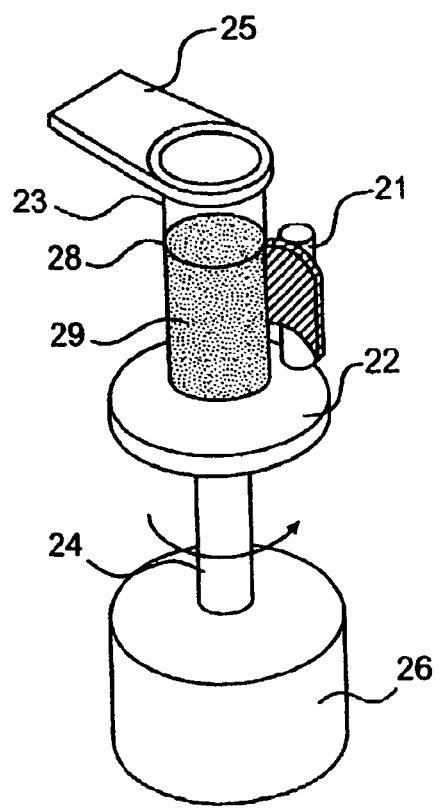
FIG. 2 shows a perspective of an alternate preferred embodiment of the invention, which includes a mobile magnet placed next to a stationary container partially filled with a liquid test medium containing magnetic particles.
Figure 3:
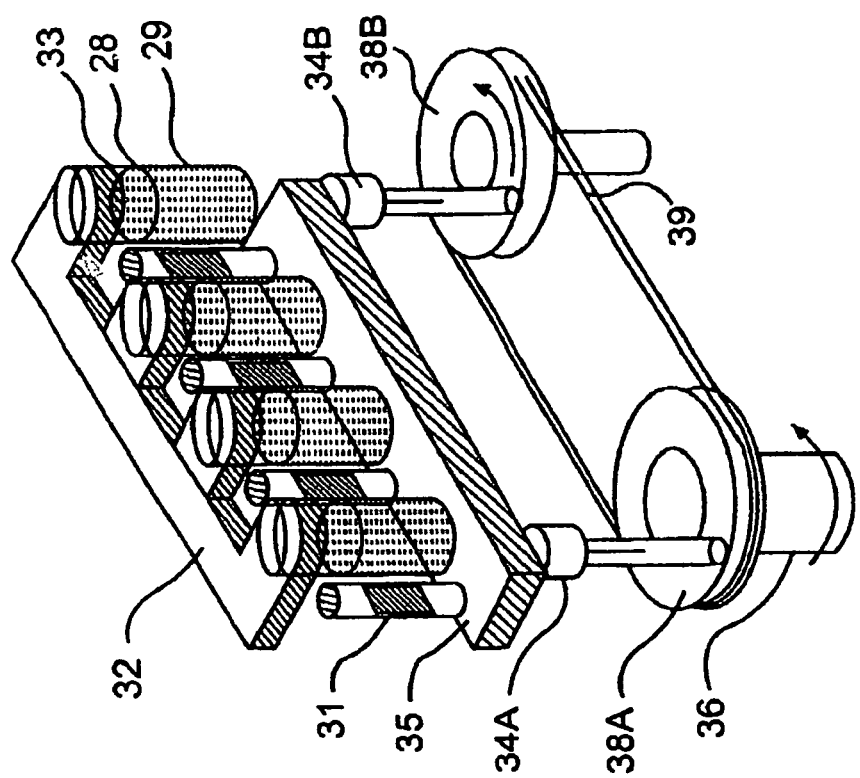
FIG. 3 shows a perspective of another preferred embodiment of the invention, which includes a row of mobile magnets placed next to corresponding stationary containers, which are rotationally displaced by a common mechanism.

In the case of moving magnets as shown in FIGS. 2 and 3 where the container(s) remains stationary, the rotating magnets may be simultaneously moved along the vertical axis of the stationary container by providing a hole in the rotatable support 22 (FIG. 2), support 22 being mounted on a hollow shaft electric motor which is available from EAD Motors, 1 Progress Drive, Dover, N.H., U.S.A., and the motor itself being mounted on a motorized linear slide mechanism such as shown in FIG. 12. The internal diameters of the hole in support 22 (FIG. 2) and the hollow shaft of the electric motor will be larger than the container 29 outer diameter. Hence the hollow shaft rotates and passes freely from one end of the container to the other. Similarly, in the case of FIG. 3, appropriately positioned holes may be provided on the support 35. The internal diameters of the holes in support 35 are sufficiently large so that the support 35 rotates freely around the containers and the length of the support shafts 34A and 34B (FIG. 3) mounted on pulleys 38A and 38B will be sufficiently long to accommodate the length of the containers. The entire rotation assembly as shown in FIG. 3 may be mounted on a motorized linear slide mechanism such as shown in FIG. 12.

FIG. 1 illustrates an apparatus for mixing and separating magnetic particles according to the present invention, which includes a magnet 1 next to a container 3. The magnet 1 is adjustably fixed to a solid support 2 without extending to the container's bottom end. The magnet 1 is preferably movable with respect to the container 3 to adjust the magnetic field strength as desired. In the preferred embodiment, the container 3 is a test tube used for holding a liquid medium 8 with magnetic particles 9 shown as small dots located in the medium. If the magnet 1 is a permanent magnet, it preferably comprises a rare earth composite type such as Neodymium-Iron-Boron or Samarium-Cobalt and has a surface field strength of about 200 Gauss to 5 kilo Gauss, which is sufficient to attract the magnetic particles in the size range of about 0.1 μm to 10 μm. The permanent magnet employed has dimensions and geometries that define a magnetic field cavity of a desired field strength having a desired cross-section within the liquid test medium 8 in the container 3. An electromagnet of comparable field strength may be used for the magnet 1.

The container 3 with the liquid medium 8 and the magnetic particles 9 is removably placed in a vertical position in a holder 5. The holder 5 is fixed to a rotating shaft 4, which is in turn attached to a variable speed electric motor 6. The holder 5 has vertical slits 7 which are elastic, to receive and firmly grip the container 3 in a vertical position. The electric motor 6 rotates the container 3 causing the relative angular position of the aggregating magnetic particles 9 in the container 3 with respect to the magnet 1 to be continuously altered, thereby inducing the magnetic particles 9 to move within the cavity of the magnetic field gradient defined within the test medium 8.

The motor 6 may be an electric step motor instead of a continuous rotation motor to provide a step-wise change of a predetermined distance in the relative angular position. Step movements of a predefined angle may be repeated more than once, and if desired, with time delays from a fraction of a second to tens of seconds between each step. Such step rotation would be accomplished by an electronic motor control that is well known in the art. Other means for effecting step-wise motion and time-delays well known in the electro-mechanical art could also be used.

The container 3 when rotated continuously is rotated from a resting position to a speed, preferably between about 50 and 200 rpm in less than one second. This speed ensures the agitation of the magnetic particles 9, while the liquid test medium 8 inside remains relatively stationary with respect to container 3. Switching off the electric motor 6 stops rotation of the container 3. The magnetically-induced agitation of the magnetic particles 9 stops and the magnetic particles 9 are attracted to and immobilized at the inside wall of the container 3 closest to the magnet 1. At this time, if desired, magnet 1 may be moved closer to container 3 to tightly aggregate the magnetic particles 9 on the vertical side of the container 3 to facilitate clean removal of the liquid test medium 8.

FIG. 2 illustrates an alternate preferred embodiment for mixing and separating magnetic particles according to the present invention which includes a test tube 23 removably inserted through an opening in a test tube holder 25 without extending to a rotating support 22. Magnet assembly 21 is adjustably fixed to rotatable support 72 without extending to the test tube's bottom end. The magnet assembly 21 may be moved or fixed at a desired distance with respect to container 23 to adjust the magnetic field strength. The magnet 21 may be either an electromagnet or a permanent magnet. If the magnet 21 is a permanent magnet, it is preferably comprised of a rare earth composite such as Neodymium-Iron-Boron with a surface field strength of about 200 Gauss to 5 kilo Gauss, sufficient to attract the magnetic particles in the size range of about 0.1 µm to 15 µm. The magnet 21 may comprise one or more magnets of suitable dimensions and geometries so as to define a magnetic field cavity of a desired field strength having a desired cross-section within the liquid test medium 28 in the test tube 23.

The rotatable disc 22 is mounted to a shaft 24, which is in turn attached to a variable speed electric motor 26. The electric motor 26 rotates the magnet 21 orbitally around the vertical axis of the stationary test tube 23 creating an angularly moving magnetic field gradient within the test medium 28. The test tube 23 remains motionless while the magnetic field cavity rotates continuously through the stationary test medium 28. The motor 26 may be an electric step motor to provide a step-wise change of a predetermined distance in the relative angular position such as described above.

The magnet when rotated continuously is rotated from a resting position to a speed, preferably between about 50 and 200 rpm in less than one second. The angularly moving magnetic field with respect to the aggregating magnetic particles 29 induces the magnetic particles 29 to move within the magnetic field cavity through the relatively motionless liquid test medium 28. When the electric motor 6 is switched off, the magnetically induced agitation stops. The magnetic particles 29 in the now stationary magnetic field are attracted to and immobilized on the inside wall of the test tube 23 closest to the magnet 21. At this time, if desired, the magnet 21 may be moved closer to test tube 23 to tightly aggregate the magnetic particles 29 on the vertical side of the test tube 23 to facilitates a cleaner removal of the test medium 28. Aggregation of the magnetic particles 28 on the vertical side of the test tube 23 facilitates removal of the test medium 28 by aspiration or other means.

FIG. 3 illustrates another preferred embodiment of the present invention for processing a plurality of test media simultaneously and is a variant of the embodiment of FIG. 2. The apparatus comprises a row of identical test tubes 33, fixed in vertical positions by their top ends passing through corresponding openings in a fixed horizontal support plate 32. The vertical position of the corresponding row of multiple magnets in a magnet assembly 31 is adjustably fixed without extending to the bottom ends of the test tubes 33. The magnet assembly 31 may be moved to and fixed at a desired distance from the test tubes 33 to adjust the magnetic field strength. If permanent magnets are used, they are preferably of a rare earth type as described above, and are selected to have suitable dimensions and geometries to define a magnetic field cavity with a desired field strength having a desired cross-section within the liquid test medium 29 in each test tube 33.

A support plate 35 for the magnet assembly 31 is fixed at its extremities by two shafts 34a and 34b. These shafts are eccentrically attached to pulleys 38a and 38b, which are, in turn, connected by a drive belt 39. The pulley 38a is attached to a variable speed electric motor 36. The motor 36 rotates the pulleys 38a and 38b, thereby imparting an eccentric rotation to support plate 35. This motion causes each magnet of the magnet assembly 31 to orbit around the vertical axes of its corresponding stationary test tube 33, thereby creating a separate moving magnetic field gradient within the motionless test media 28 of each test tube 33. The motor 36 may be an electric step motor to provide a step-wise change of a predetermined value in the relative angular position such as described above.

The magnets when rotated continuously are rotated from a resting position to a speed, preferably between about 50 and 200 rpm in less than one second. The simultaneous movement of multiple magnetic fields induces the aggregating magnetic particles 29 in each test tube 33 to move within their individual cavities of the magnetic field gradient. Stopping the electric motor 36 stops the rotation of the magnet assembly 31 and stops the magnetically induced agitation. The magnetic particles 29, in the stationary magnetic fields are attracted to and immobilized on the inside walls of each test tube 33. If desired, magnet assembly 31 may be moved closer to test tubes 33 to tightly aggregate the magnetic particles 29 on the vertical sides of the test tubes 33 to facilitates a cleaner removal of the test medium 28. The separation of magnetic particles on the vertical side of the test tubes 33 facilitates removal of the supernatant liquid media by aspiration or other methods.

Figure 4:
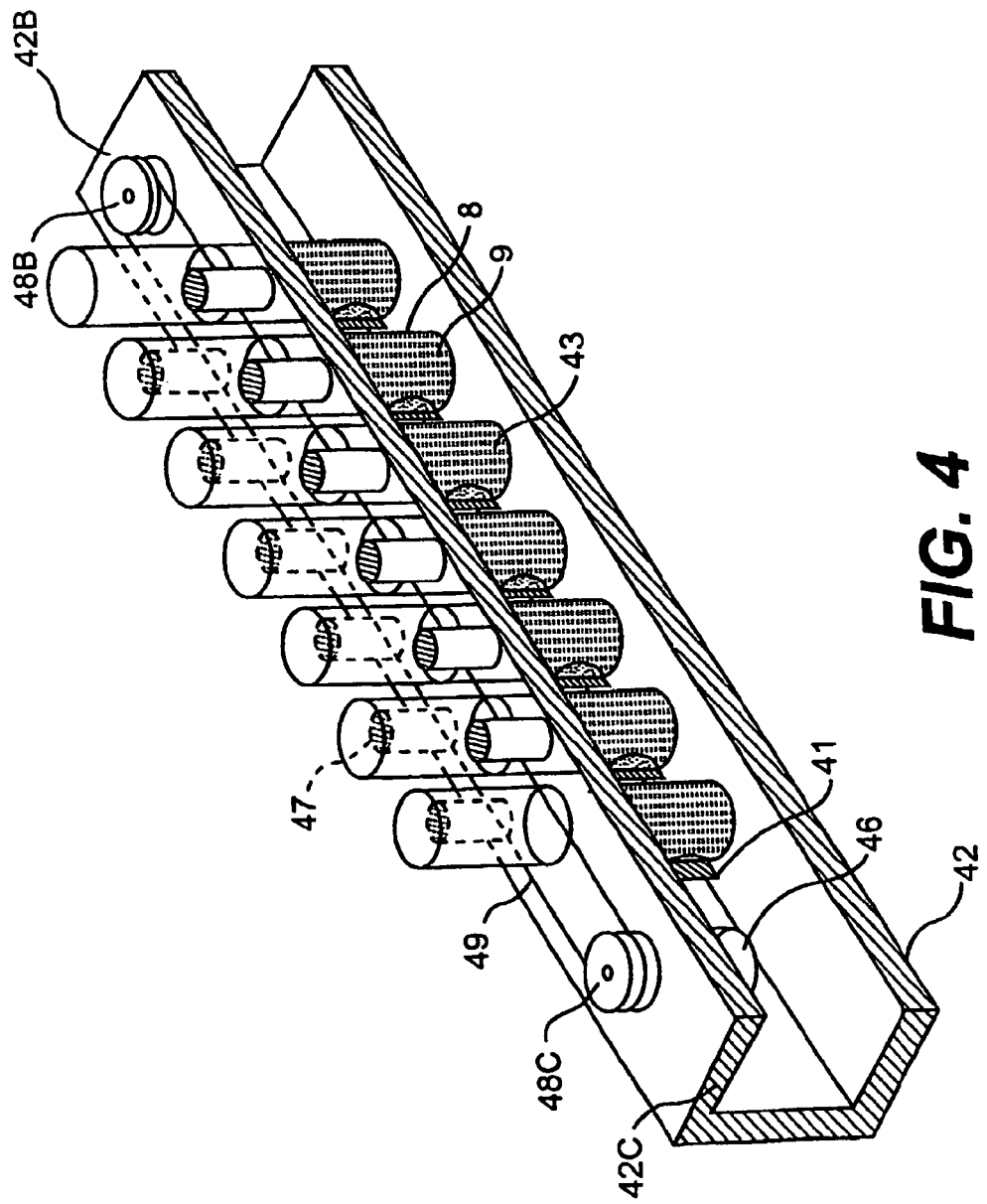
FIG. 4 shows a perspective of another preferred embodiment of the invention, which includes a row of stationary magnets placed next to corresponding rotatable containers, which are rotated by a common mechanism.

FIG. 4 illustrates another preferred embodiment of the present invention for processing a plurality of test liquid media simultaneously, and is a variant of the embodiment of FIG. 1. The apparatus comprises a row of multiple magnets 41, fixed on a support plate 41b (not shown). The support plate is preferably adjustably mounted to align the row of magnets so each magnet corresponds with its respective test tube 43. Support plate 41b also preferably provides lateral movement to adjust the distance between the magnet assembly 41 and the row of test tubes 43. The magnets 43 thus can be moved to a desired distance from the test tubes 43 to adjust the magnetic field strength. If permanent magnets are employed, they are preferably a rare earth type as described above and have dimensions and geometries so as to define a magnetic field cavity which accommodates a desired cross-section within the liquid test medium 8 in each test tube 43.

The test tubes 43 are removably placed in vertical positions with their bottom ends resting in a row of shallow grooves on a bottom plate 42. A portion of their top ends pass through corresponding openings in an upper plate 42b of the test tube rack 42. The diameter of the openings in the upper plate 42b is slightly larger than the diameter of the test tubes 43 so that they can be readily inserted and freely rotated. The plates 42 and 42b are spaced apart so as to hold the test tubes 43 in a stable vertical orientation.

A drive belt 49 is mounted on two pulleys 48b and 48c. Pulley 48c is attached to a variable speed motor 46, and guided by two parallel rows of guidance rollers 47 mounted on the top plate 42b. The guidance rollers 47 are positioned between the rows of openings to slightly pinch the drive belt 49 so that the drive belt 49 grips the upper ends of the test tubes 43. Motor 46 moves the drive belt 49. The linear sliding friction of belt 49 against the external surface of each test tube simultaneously rotates all test tubes 43 around their vertical axes. The motor 46 may be an electric step motor to provide a step-wise change of a predetermined distance in a relative angular position, such as described above.

At a suitable acceleration, test tubes 43 rotate, the relative angular position of the aggregating magnetic particles 9 in each one of the test tubes 43 and its corresponding magnet 41 is continuously altered. This induces the magnetic particles 9 to move within the cavity of the magnetic field gradient. The test tubes 43 are rotated from resting position to a speed, preferably between about 50 and 200 rpm in less than one second to ensure the agitation of the magnetic particles 9 while maintaining the test media 8 inside relatively stationary. Stopping the electric motor 46 stops rotation of test tubes 43 and the magnetically induced agitation. The magnetic particles 9 in each test tube 43 are now attracted to and immobilized at the inside wall closest to the magnets 41. The aggregation of the magnetic particles 9 on the vertical side of the test tubes 43 facilitates removal of the test medium 8 by aspiration or similar methods. If desired, magnet assembly 41 may be moved closer to container 23 to tightly aggregate the magnetic particles 9 on the vertical side of the container 43 to facilitates a dean removal of the test medium 8.

An instrument incorporating the above-described principles of the invention has been built and is being sold by Sigris Research, Inc., P.O. Box 968, Brea, Calif. 92622. Literature describing the operation of the instrument, specifications and actual performance statistics widely distributed since 1996 is available from Sigris Research, Inc. and is incorporated herein by reference.

FIG. 12 illustrates another preferred embodiment of the present invention for processing a plurality of test liquid media simultaneously. It includes a linear drive mechanism mounted on a positioning mechanism and a rotation mechanism. The three mechanisms allow vertical linear movement of a magnet assembly, adjustment of the distance between the magnet assembly and containers, and rotation of the containers. Simultaneous container rotation and linear magnet movement provides the advantage of processing large volumes of test media with a relatively small quantity of magnetic particles.

The apparatus of FIG. 12 consists of two main pans, linear drive assembly 111 and base assembly 112. Both assemblies are constructed of a nonmagnetic material, aluminum being preferred. The linear drive assembly 111 comprises a rigid frame 113 with two fixed guide rods 114 and 115 and a centrally located screw shaft 116. The end portions of screw 116 are smooth and un-threaded and are mounted in two centrally located ends flanges (not shown). The screw 116 is freely rotatable and includes a roll nut (not shown) which moves linearly in the vertical plane, either up or down, upon rotation of screw 116. A pulley 117 is fixed to the smooth portion of screw 116 protruding from the top plate 136 of frame 113 and is connected by a timing belt 118 to another pulley 119 fixed to the shaft of a variable speed electric motor 120 mounted on bracket 121 of frame 113. Timing belt 118 is made of neoprene or urethane with precisely formed grooves on the inner side. The belt width and groove pitch match the dimensions of the teeth on pulleys 117 and 119 to provide positive and non-slip power transmission. Suitable timing belts and gear pulleys may be obtained from Stock Drive Products, New Hyde Park, N.Y. or from other similar vendors.

A carriage 122 is fixed on the roll nut of screw 116. Its vertical motion is ensured by the accurately aligned guide rods 115 and 114. Linear drive assembly 111 is attached to base assembly 112 by bolting the bottom plate 139 of frame 113 to a linear slide mechanism 123. A rod with a knob 128 inserted through a center hole of the base assembly 112 is attached to the linear slide mechanism 123. The linear slide mechanism 123 thus can be moved forward or backward by pulling or pushing the knob 28 to position it at a desired distance from the containers 124.

A magnet assembly 125 with magnets 126 is removably mounted on the linear drive carriage 122 by means of three evenly spaced screws 127. This is advantageous because magnets of varying size and geometry can be easily exchanged. The magnets 126 are aligned with the row of containers 124. Their distance from the containers is adjusted by pulling or pushing the knob 128.

The motor 120 rotates the screw 116. The roll nut converts this wary motion to a linear motion moving magnet assembly 125 vertically. The direction of the linear movement of magnet assembly 125 is controlled by the clockwise or counter-clockwise rotation of the motor 120 by a motor controller. The movement of magnet assembly 125, either upward or downward can thus be controlled at will and may be repeated for as many cycles as desired.

The position and the stroke length of the linear up and down movement of the carriage 122 may be controlled by two position sensors to control the lowest and highest extremes of travel of the carriage 125. An electronic signal from these sensors may be used to reverse the motor rotation, thereby causing a repeated scanning for a desired length of the containers 124 by their corresponding magnets 126.

Electronic motor controllers and position sensor are well known in the art and may be obtained from any one of a number of vendors. If permanent magnets are employed, they are preferably a rare earth type as described above and have suitable dimensions and geometries so as to define a magnetic field cavity of a desired field strength which provides a desired cross-section within the liquid test medium in each container.

The base assembly 112 includes a mechanism for rotation comprising a variable speed electric motor 129 with a gear pulley 130 fixed to its shaft. A pulley rotor 131 is attached to each one of a plurality of holder 134. A timing belt 132 is wrapped around the gear teeth of pulley 130 and each of the rotors 131. Although only one rotor 131 is shown next to a holder 134 for a container 124, it should be understood that each container holder 134 has a rotor 131 associated with it, which is driven by the belt 132. The motor 129 and rotor pulleys 130, 131 are secured in their precise positions by a top metal plate 133 fixed to base assembly 112. It should be noted that the gear pulley rotors 131 are free rotating and their respective shafts protrude from corresponding holes in plate 133. The belt width and the inner groove pitch of the timing belt 132 dimensionally match with gear teeth of the motor gear pulley 130 and the rotors 131 to provide positive and non-slip power transmission. If desired, idling rollers may be installed between the pulleys to increase the wrap around the gear teeth for a firmer non-slip power transmission. The motor 129 rotates the timing belt 132 thereby simultaneously rotating all pulley rotors 131.

Holders 134 are removably mounted on the tapered end of a rotor shaft 135 protruding from corresponding holes in plate 133 and provide means for firmly holding containers 124 in a substantially vertical position. A removable holder design is advantageous as it provides a convenient means to accommodate a variety of container sizes on the apparatus by simply changing the holders to correspond to the container geometry.

The position of the magnet assembly 125 may be adjusted to a required distance from the row of containers 124 by pulling or pushing the knob 128. The motor 129 rotates containers 124 around their vertical axes. At a suitable angular acceleration preferably between about 1.05 to 4.19 rads/s$^2$, the relative angular position of the aggregating magnetic panicles in each container with respect to its corresponding magnet 126 is continuously altered, inducing the magnetic particles to mix within the cavity of the magnetic field gradient, as described above. While the containers 124 are rotating, motor 120 may be switched on to move the magnets 126 up and down in the vertical plane thereby moving the magnetic field cavity in alignment with the vertical axis of the containers. Upon reaching a desired length of the container, the direction of movement of magnet assembly 125 is reversed. This process is repeated for the entire duration of particle mixing necessary to bind the target species to particle surface by affinity reaction.

It will be recalled that the magnetic particles remain confined in the magnetic field cavity. Particle to target substance ratio therefore may be adjusted to relatively high levels within the magnetic field cavity to provide reaction conditions, which overwhelmingly favor affinity binding. By combining a linearly moving magnetic field cavity with the angular movement of particles confined within the magnetic field cavity, a simple and efficient means to process large volumes of test media without a concomitant increase in particle concentration is obtained. This was not heretofore possible.

The motor 129 may be an electric step motor to provide a step-wise change of a predetermined distance in the relative angular position such as described above. Similarly, motor 120 may be an electric step motor to provide a step-wise change of a predetermined distance in the vertical plane. Various combinations of continuous and step-movement for the rotation and linear movement may be utilized. In every case the optimum speed of rotation and linear movement will be determined by trial and error.

For separation, the linear drive motor 120 is turned off. The magnet assembly 125 is brought to a home position. The rotation drive motor 23 is turned off. The magnetic particles in the containers 124 are attracted to and immobilized at the inside wall closest to the magnets 126. The aggregation of the magnetic particles on the vertical side of the container 124 facilitates removal of the test medium by aspiration or similar methods. If desired, magnet assembly 125 may be moved closer to containers 124 by moving knob 128. This tightly aggregates the magnetic particles on the walls of the containers 124 to facilitate a clean removal of the test medium.

FIGS. 5a through 5f illustrate the preferred steps in a method practiced by the preferred embodiments described above, using affinity reactive magnetic particles of about 2.8 μm for the purpose of bioassays, or for the isolation of cellular or molecular species from a sample solution or suspension of biological fluids.

Figure 5C:
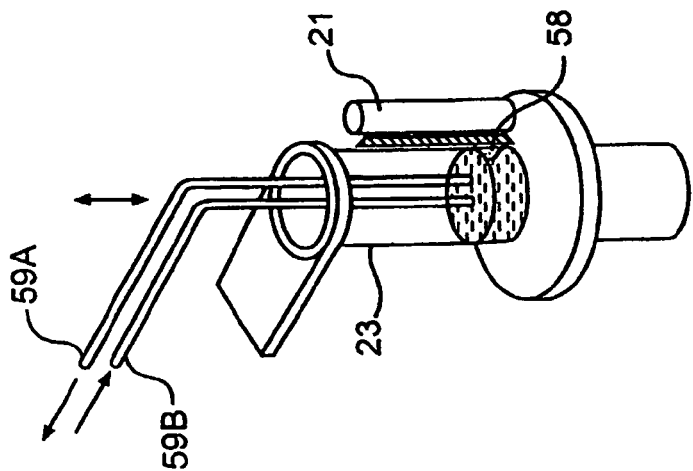
FIGS. 5a, 5b, 5c, 5d, 5e and 5f schematically illustrate the steps of a method according to the invention for mixing and separation of a target substance employing magnetic particles using the preferred embodiment of FIG. 2.
Figure 5B:
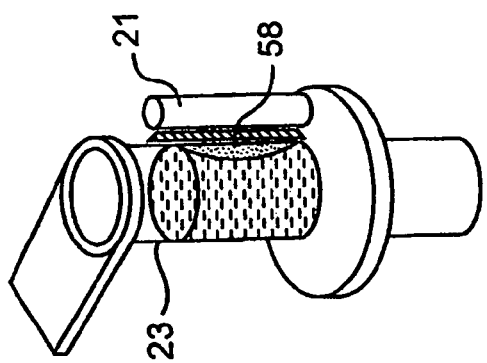
Figure 5A:
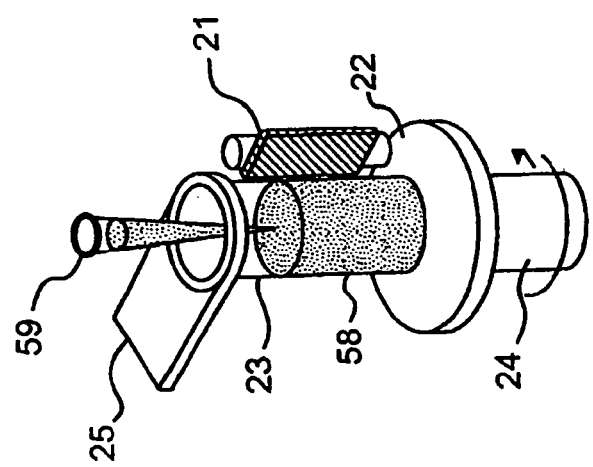

FIG. 5a shows an apparatus of FIG. 2, in which a suspension of magnetic particles 58 in a sample solution is dispensed with a pipette 59c into a test tube 23 of about 10 mm diameter. A magnet 21 of about 45 MGOe is moved to a distance of about 5 mm from test tube 23 so as to a create a field of about 600 Gauss in the center of the test tube. This preferred distance is determined by measuring the magnetic field inside the tube by a magnetometer. The motor is turned on and the magnetic particles 58 are mixed by rotating the magnet 21 around the test tube 23. FIG. 5b shows the same apparatus when mixing is completed, rotation of the magnet 21 has stopped, and the magnet is moved closer to the test tube 23. The magnetic particles 58 are immobilized against the inner wall of test tube 23 closest to the stationary magnet 21.

FIG. 5c shows the apparatus during a washing step. In this step, an outlet tube 59a aspirates the supernatant test medium and an inlet tube 59b adds a suitable wash solution into the test tube 23. The magnetic particles 58 are then mixed in the wash solution. The old wash solution is aspirated and new clean solution may be added. The washing step may be repeated as many times as required.

Figure 5D:
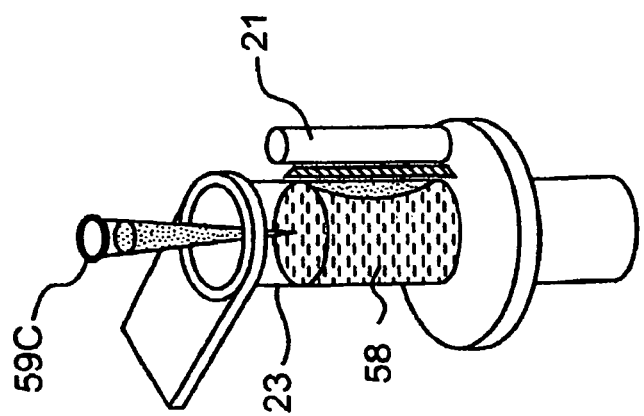

FIG. 5d shows the apparatus stopped for the addition of one or more reagent solutions by pipette 59c for effecting a desired analytical reaction for a bioassay or a chemical displacement reaction to elute the target substance from the magnetic particles 58.

Figure 5E:
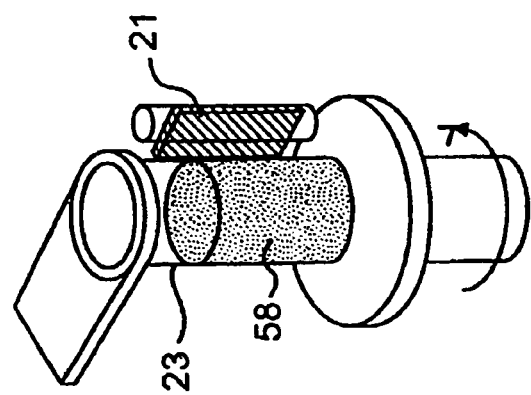

FIG. 5e shows the same apparatus turned on for dispersing and mixing the magnetic particles 58 for carrying out the desired reaction.

Figure 5F:
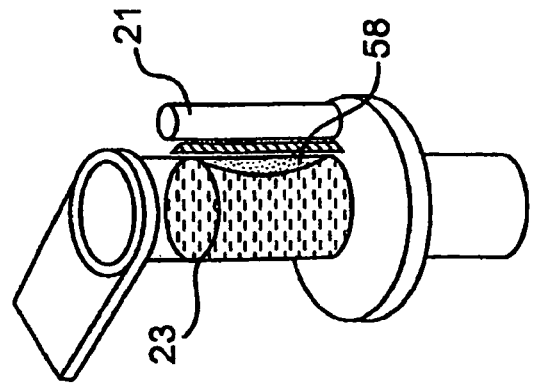

FIG. 5f shows the apparatus stopped to separate the magnetic particles 58 from the reaction medium. In the case of bioassays, the supernatant liquid may be measured by any desired measurement method, either directly in test tube 23 or by transferring it elsewhere. For the purpose of isolating a cellular or molecular species, the supernatant may be transferred to a suitable container for subsequent treatment as desired. Examples of actual separations of mRNA and protein are described in a technical brochure entitled "MixSep", obtainable from Sigris Research, Inc., and are incorporated herein in its entirety.

Figure 6:
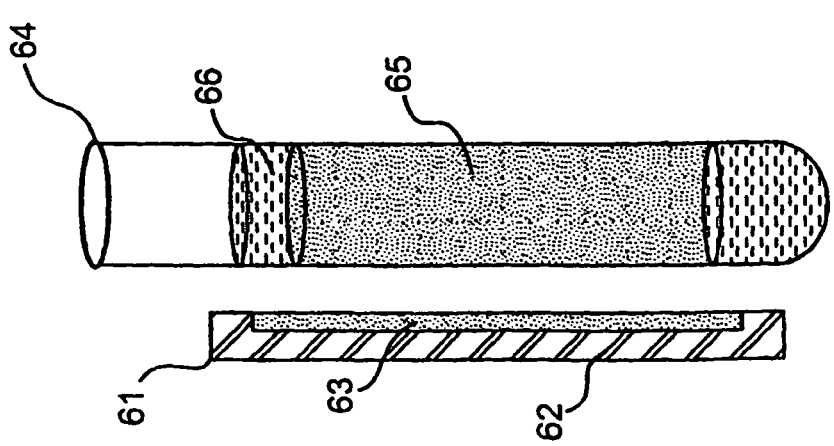
FIG. 6 shows a perspective view of a magnetic field gradient cavity in a test liquid medium according to the invention caused by one permanent magnet placed close to the container.

Various preferred configurations of magnet assemblies and their position with respect to a container will now be described with reference to FIGS. 6 through 9. FIG. 6 shows a perspective view of an embodiment of the magnet assembly 61 according to the invention wherein a rectangular permanent magnet 62 is fixed on a nonmagnetic base 63 and placed in proximity to a container 64 to generate a cavity of magnetic field gradient 65 in a cross-section of a liquid test medium 66. The usable magnetic field remains mostly confined within this cavity, i.e., there is negligible field strength outside the cavity.

Figure 7:
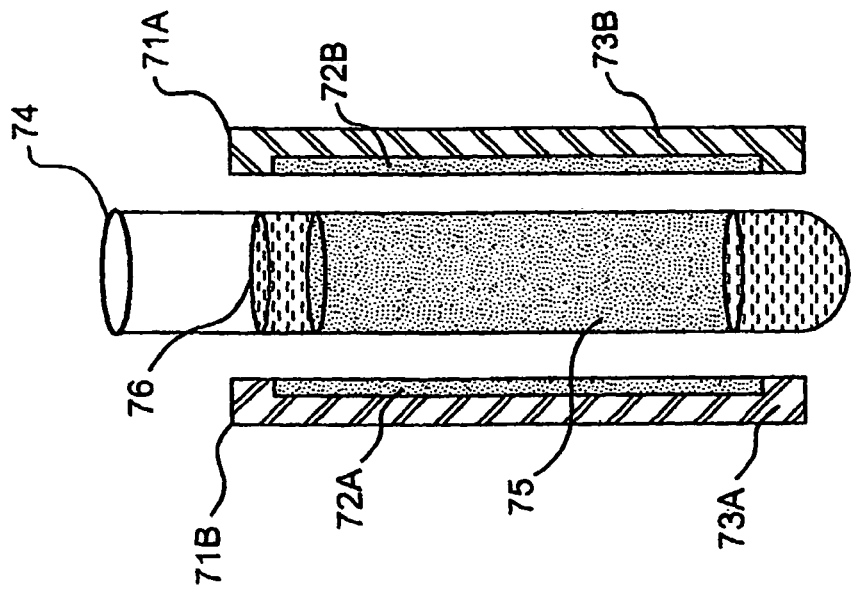
FIG. 7 shows a perspective view of a magnetic field gradient cavity in a liquid test medium according to the invention caused by two magnets placed at the opposite sides of the container.

FIG. 7 shows two magnet assemblies, 71a, 71b, each comprised of two rectangular permanent magnets 72a and 72b fixed on two nonmagnetic bases 73a and 73b, respectively. The two magnet assemblies 71a, 71b are located on the opposite sides of a container 74 with similar magnetic poles facing each other to distort the magnetic flux lines and generate a cavity of magnetic field gradient 75 in the liquid test medium 76 and two loci of magnetic force in the cavity 75 as explained above (see FIG. 11a). Such an arrangement may be particularly effective for mixing magnetic particles.

Figure 8:
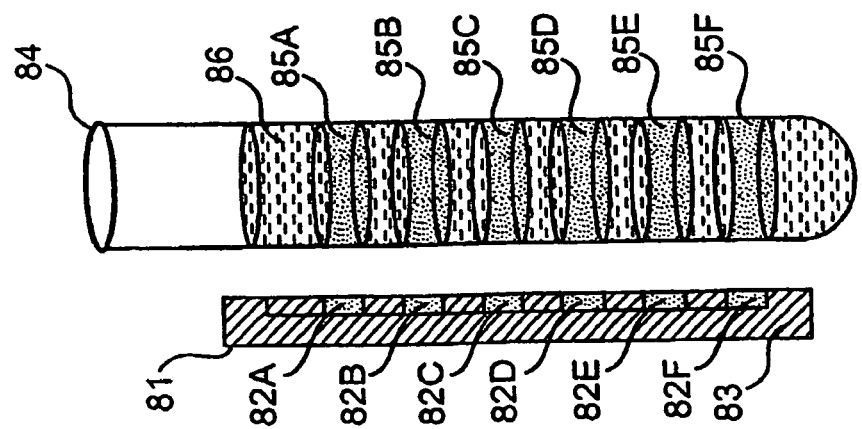
FIG. 8 shows a perspective view of multiple magnetic field gradient cavities in a liquid test medium according to the invention caused by a vertical array of six permanent magnets placed close to the container.

FIG. 8 shows a magnet assembly 81 designed to generate multiple cavities of magnetic field gradient in a container 84. An array of six rectangular permanent magnets 82a to 82f fixed on a nonmagnetic support frame 83 is preferred. Magnets 82a to 82f are vertically mounted on the non-magnetic support 83 wherein each magnet is substantially separated by a non-magnetic spacer and like poles over like poles so that magnetic flux lines from each magnet traversing the test medium 86 are mutually repulsive and generate a plurality of distinct magnetic field cavities. The spacing between magnets should be such as to prevent the intermixing of magnetic particles from one field cavity to other. Such spacing may be even or uneven.

The magnet assembly 81 is placed at a desired distance from the container 84 to generate six separate cavities of magnetic field gradient 85*a* to 85*f* in a liquid test medium 86. Such multiple magnetic field cavities are useful for isolating a multiple of target substances from a test medium in a single operation. The affinity magnetic particles in a given cavity will specifically bind a given target substance only. Specific types of magnetic particles are added sequentially from bottom cavity to top cavity. In the first step, the container is filled with a suspending solution to the level of the first cavity, magnetic particles are then added and allowed to aggregate. This step is repeated until all cavities are filled with the desired type of magnetic particles. The suspending solution, is then removed and the container filled with the test medium. Alternatively, a test liquid sample may be layered over the test medium and the target substance allowed to settle down by gravitational force while the particles are mixing. Such a method is of particular use for isolating different cellular components in a single process. Mixing and separation are then carried out as described in connection with FIG. 5.

Figure 9:
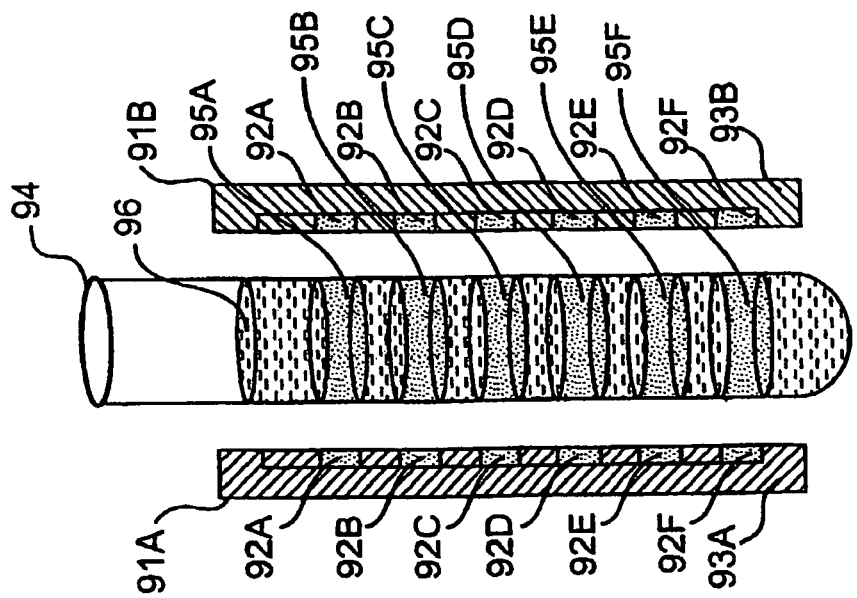
FIG. 9 shows a perspective view of multiple magnetic field gradient cavities in a liquid test medium according to the invention caused by two vertical arrays of permanent magnets placed at the opposite sides of the container.

FIG. 9 shows two magnet assemblies 91*a* and 91*b*, each comprising an array of six evenly-spaced rectangular permanent magnets 92*a* to 92*f* fixed on two nonmagnetic support frames 93*a* and 93*b*, respectively. The spatial and pole arrangements of assemblies 91*a* and 91*b* are similar to the one described in FIG. 8. The two magnet assemblies 91*a* and 91*b* are located on the opposite sides of a container 94 with like magnetic poles facing each other. Six cavities of magnetic field gradient 95*a* to 95*f* thus generated in a test medium 96 by distorted magnetic flux lines of two operative magnetic fields in each cavity.

The various configurations of magnet assemblies and position as described above may be advantageously employed in the embodiments of the invention depicted in FIGS. 1 to 4 and 12.

Figure 10A:
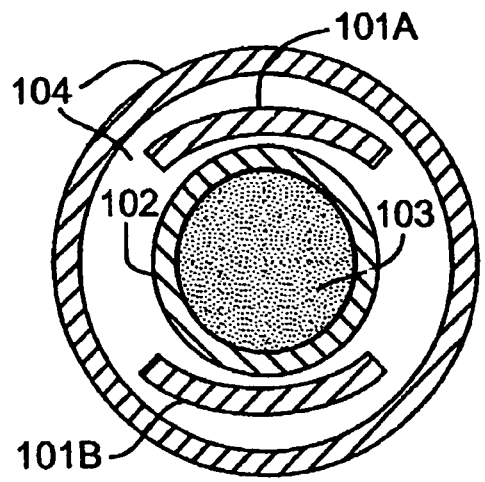
FIG. 10a shows a perspective top view of another preferred embodiment of the invention, which includes two electromagnets placed at opposite sides of the container.
Figure 10B:
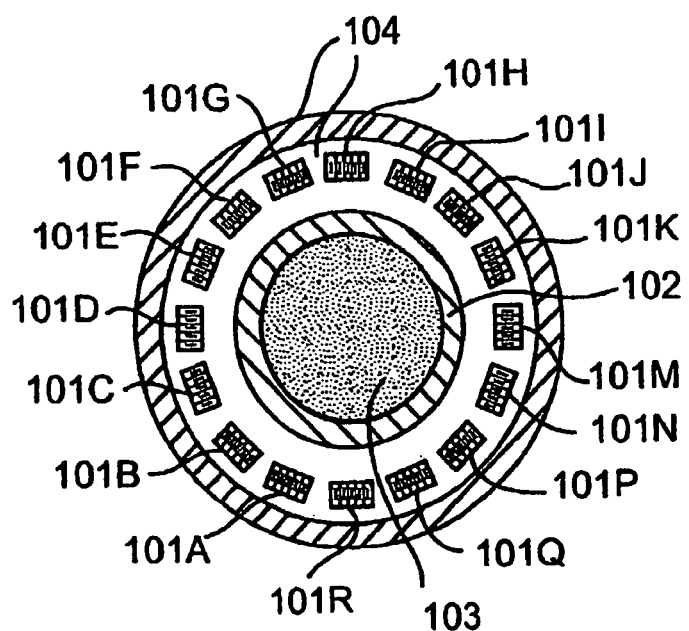
FIG. 10b shows a perspective top view of yet another preferred embodiment of the invention, which includes a ring of electromagnets surrounding the container.

As mentioned above, permanent magnets and electromagnets are interchangeable in most configurations of the present invention. However, those configurations that require movement of a magnet are more easily realized with permanent magnets. Electromagnets require commutators or other arrangements to conduct electricity to the moving magnets. There are certain unique configurations in which electromagnets are greatly preferred. FIG. 10*a* shows two electromagnet coils 101*a* and 101*b* mounted on a support frame 104 and displaced at about 180 degrees at the exterior of a container 102 with the liquid test medium and magnetic particles 103 inside. FIG. 10*b* shows a cross-section of a single container 102 with the liquid test medium and magnetic particles 103 surrounded by a ring of individual electromagnet coils 101*a* to 101*r* mounted on a support frame 104.

Here neither the container 102 nor the electromagnets 101 actually move. Instead, angular movement is induced in the magnetic particles suspended within the test medium 103 inside the container 102 by sequentially energizing the electromagnets. This sequential energization may be "binary" (i.e., on and off) or "analog," in which a first electromagnet is gradually fully energized, and then has its power reduced, while the next electromagnet is gradually energized, and so on. It will be apparent that rate of motion of the magnetic particles 103 can be modulated by the rate of change and the degree of overlap between the sequential electromagnets.

The exact number of sequential electromagnets employed will depend on the size of the container 102 and other parameters. FIG. 10*a* shows that this configuration reduces to a configuration not unlike that of FIG. 7, but with two opposed electromagnets rather than two permanent magnets. The angular movement from one magnet to the other in its simplest form is 180 degrees so that the magnetic particles in the test medium 103 will move in relatively straight lines back and forth across the container 102. More variety is preferably added to the paths of the magnetic particles by modulating the polarity, as well as the power level of the electric current, thereby altering the direction of the magnetic poles with alterations of the magnetic field corresponding to those shown in FIGS. 11*a* and 11*b*.

It has been found that a configuration employing four electromagnets equally spaced (i.e., 90 degrees apart) around a container can produce very acceptable agitation of magnetic particles through a judicious use of sequential activation of the electromagnets and through polarity reversals, as discussed above.

The container defining the mixing and separation chamber includes at least one opening for the addition and removal of a test medium. The container is preferably of substantially cylindrical form and made from a magnetically permeable material such as plastic or glass. Additionally, the inside surface of the chamber may be biocompatible and, if desired, the chamber may be sterilized for aseptic processing of the test media. The volume of the container is not critical as long as an adequate magnetic field gradient can be provided to accommodate the chamber and, particularly, can accommodate the desired cross-section of the liquid test medium inside.

As shown in FIGS. 1 through 9 and 12, the container used to hold the test medium may be a test tube or an eppendorf type of tube with a conical bottom. The volumetric capacity of the test tube is preferably between 250 µl to about 18 ml as usually employed in research laboratories. The various configurations of apparatus as described above can be easily scaled up to process much larger volumes of liquid test media as may be required for clinical applications. In all cases, the size and geometry of the magnet is adjusted to generate an adequate magnetic field strength within the field cavity of the test medium inside a particular size of container.

Although embodiments of the present invention particularly suited for use in the research laboratory preferably employ readily removable and replaceable containers such as test tubes, diagnostic and other devices employing the teachings of the present invention might employ permanent flow cells or other nonremovable chambers for mixing and separation.

Those skilled in the art will appreciate that various adaptations and modifications of the just-described preferred embodiment can be configured without departing from the scope and spirit of the invention wherein the affinity reactive magnetic particles are admixed with the liquid test medium in a container by effecting a relative angular movement of the magnetic particles in the liquid test medium, while the liquid remains essentially motionless. Although relative angular movement is achieved by rotating the container or orbiting the magnet, alternative mechanism will be obvious to a skilled artisan. For example, relative angular movement between the magnetic source and the aggregating magnetic particles may be effected by moving the magnet or the container by a linear motion mechanism using an appropriate linear acceleration. For this purpose, at least two magnets will be positioned diametrically opposite one another relative to the container but staggered so that the magnetic field inside the container generated by one magnet is substantially unaffected by the magnetic field generated by the other magnet. The linear acceleration of either the magnet or container will mix the magnetic particles in a manner analogous to the 180° step rotation movement described earlier.

Figure 13:
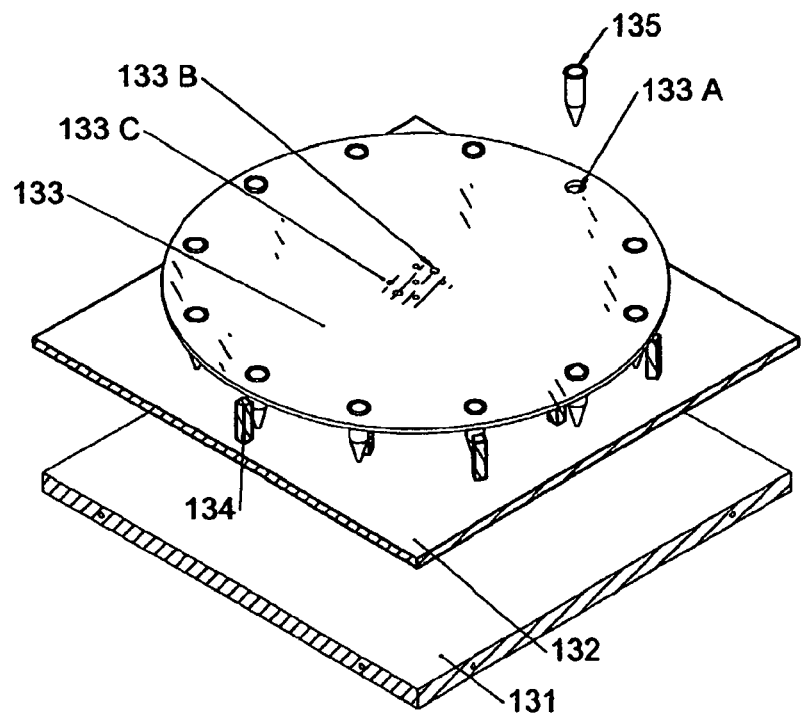
FIG. 13 A shows an isometric view of yet another alternate preferred embodiment of the invention, which includes magnets mounted in two concentric circular arrangement on a static plate and the containers inserted in a circular pattern of holes in a rotor plate which by rotation alternately positions the opposite sides of the containers in front of the each circular array of magnets.
Figure 13:
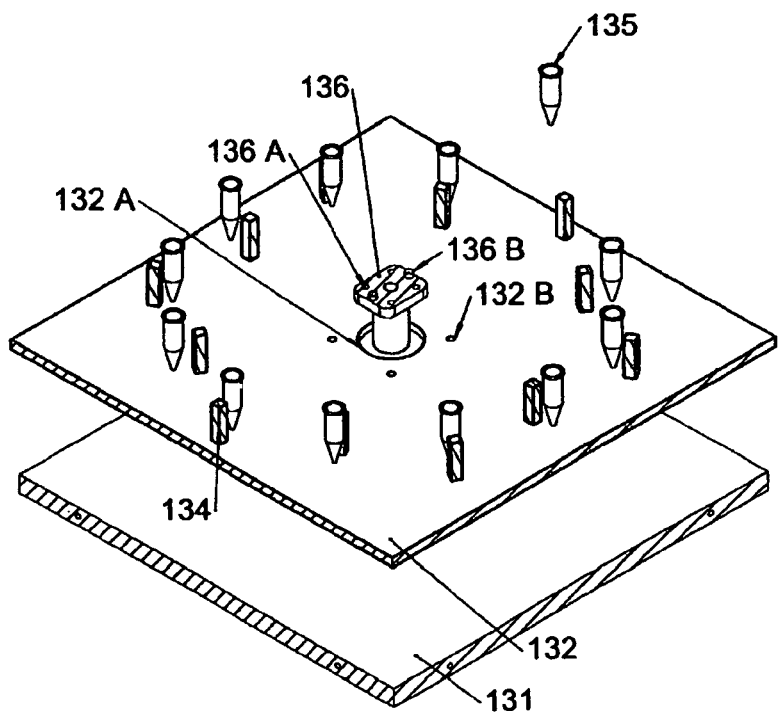
Figure 13:
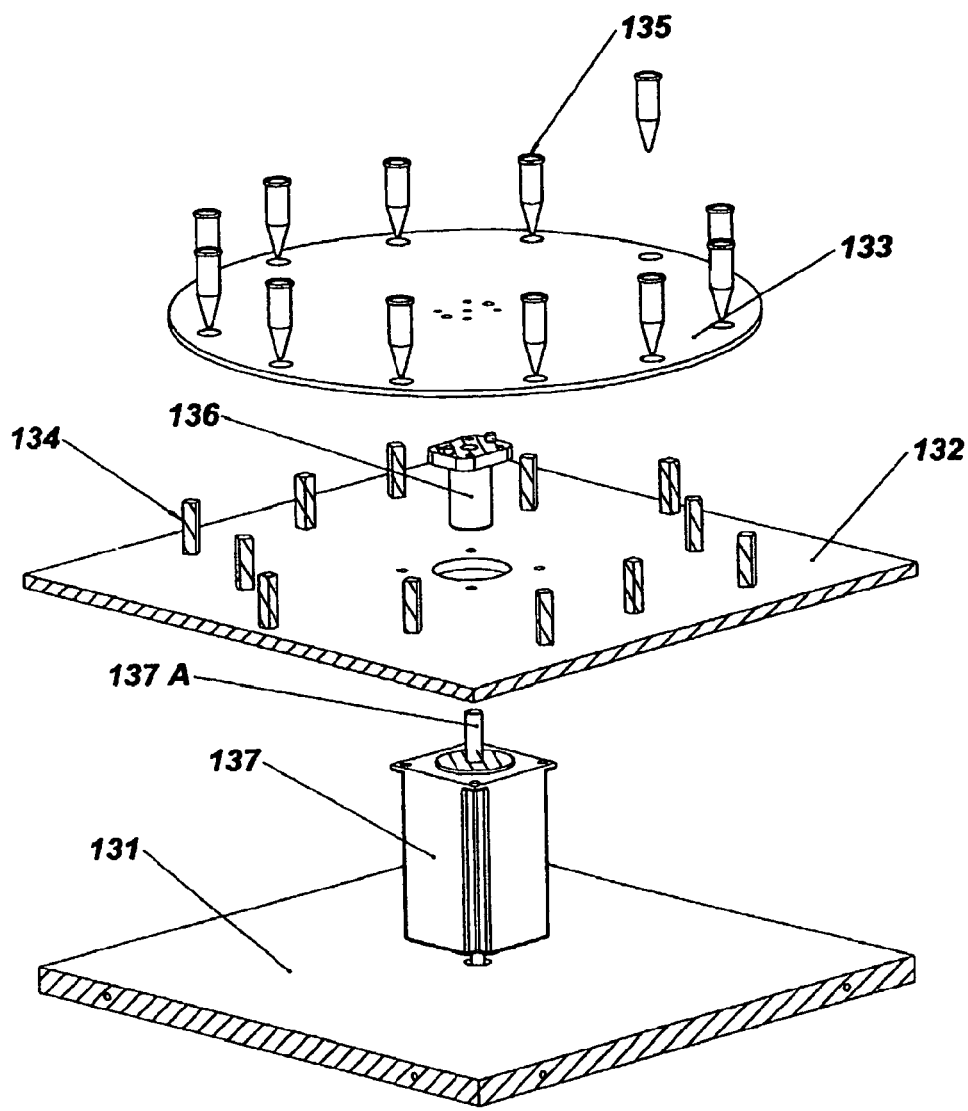
Figure 14:
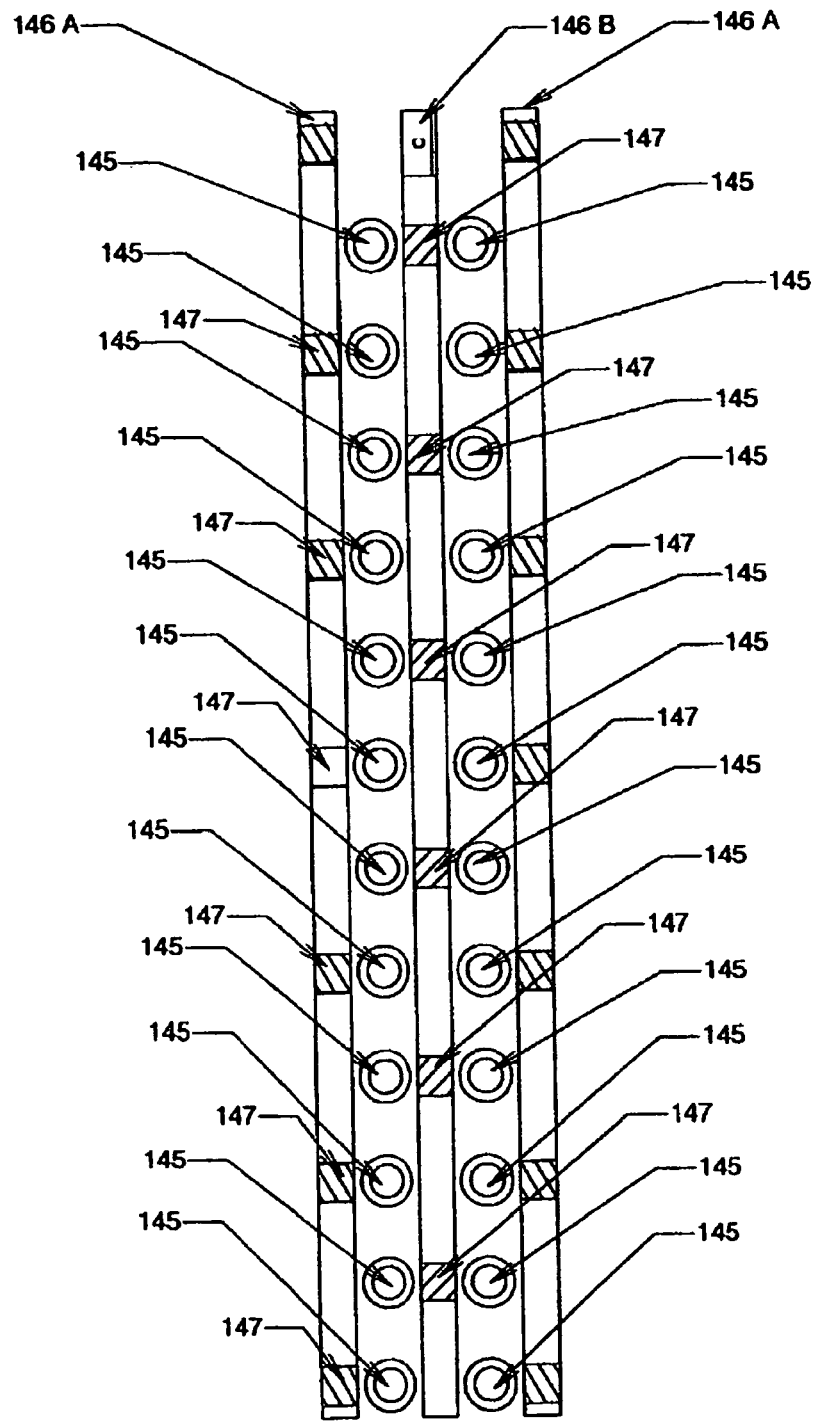
FIG. 14 A shows yet another alternate preferred embodiment of a invention which includes containers inserted in a linear pattern the holes of a static plate and a linear array of magnets mounted in a linear pattern on a moveable support plate which by horizontally moving back and forth alternately brings the magnets on the opposite sides of the containers.
Figure 15:
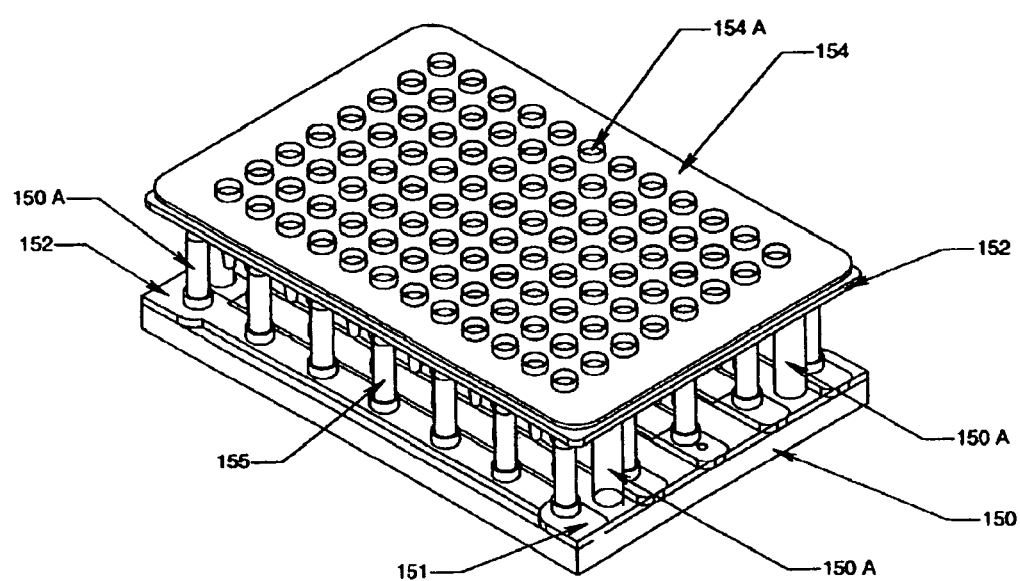
FIG. 15 shows an isometric view of yet another preferred embodiment of the invention for the 96-well microplate format containers and linear arrays of magnets mounted on two independently moveable support structures, which by alternate movements in the vertical direction bring the magnets between the wells of the 96-well microplate.
Figure 15:
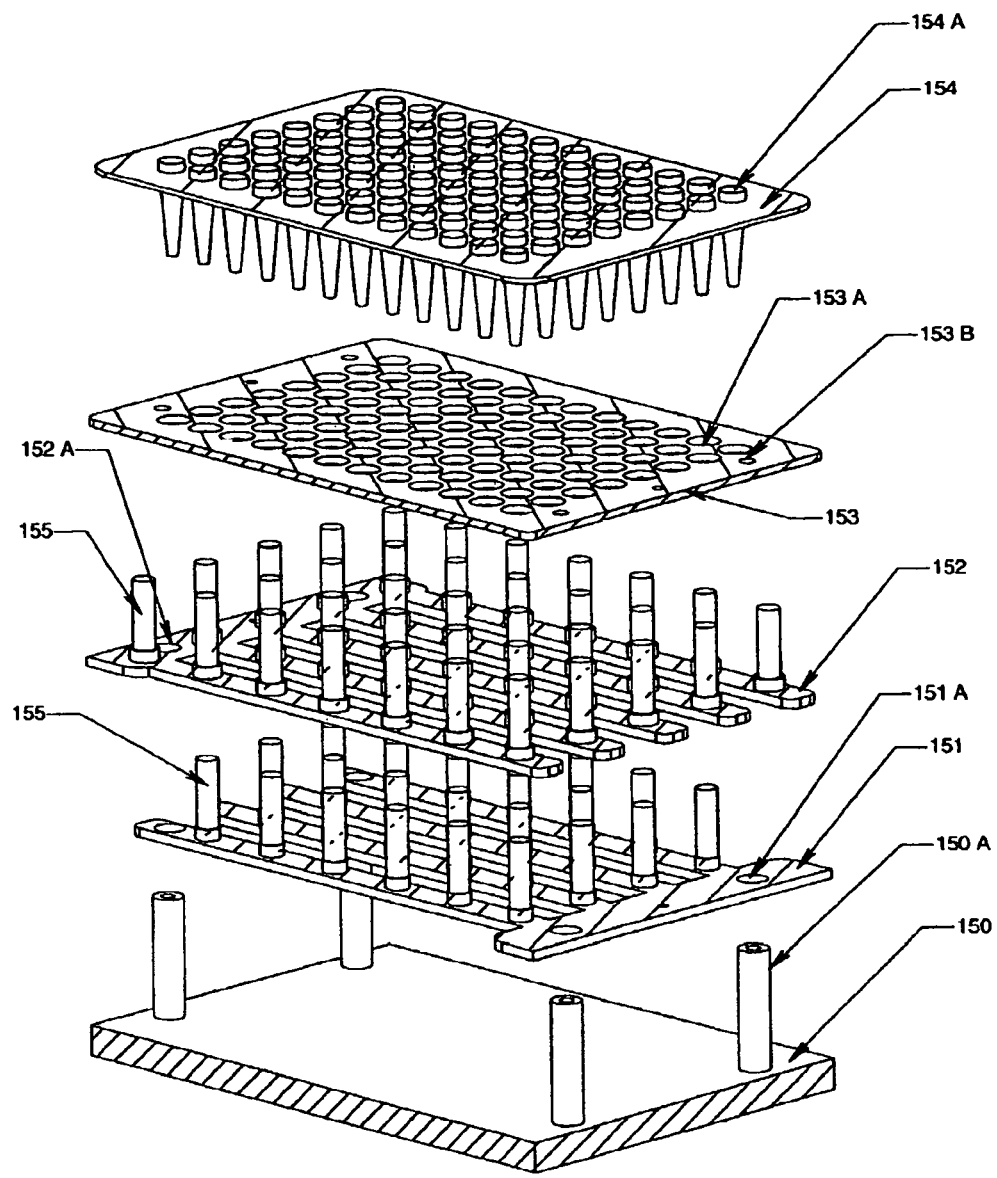
Figure 15:
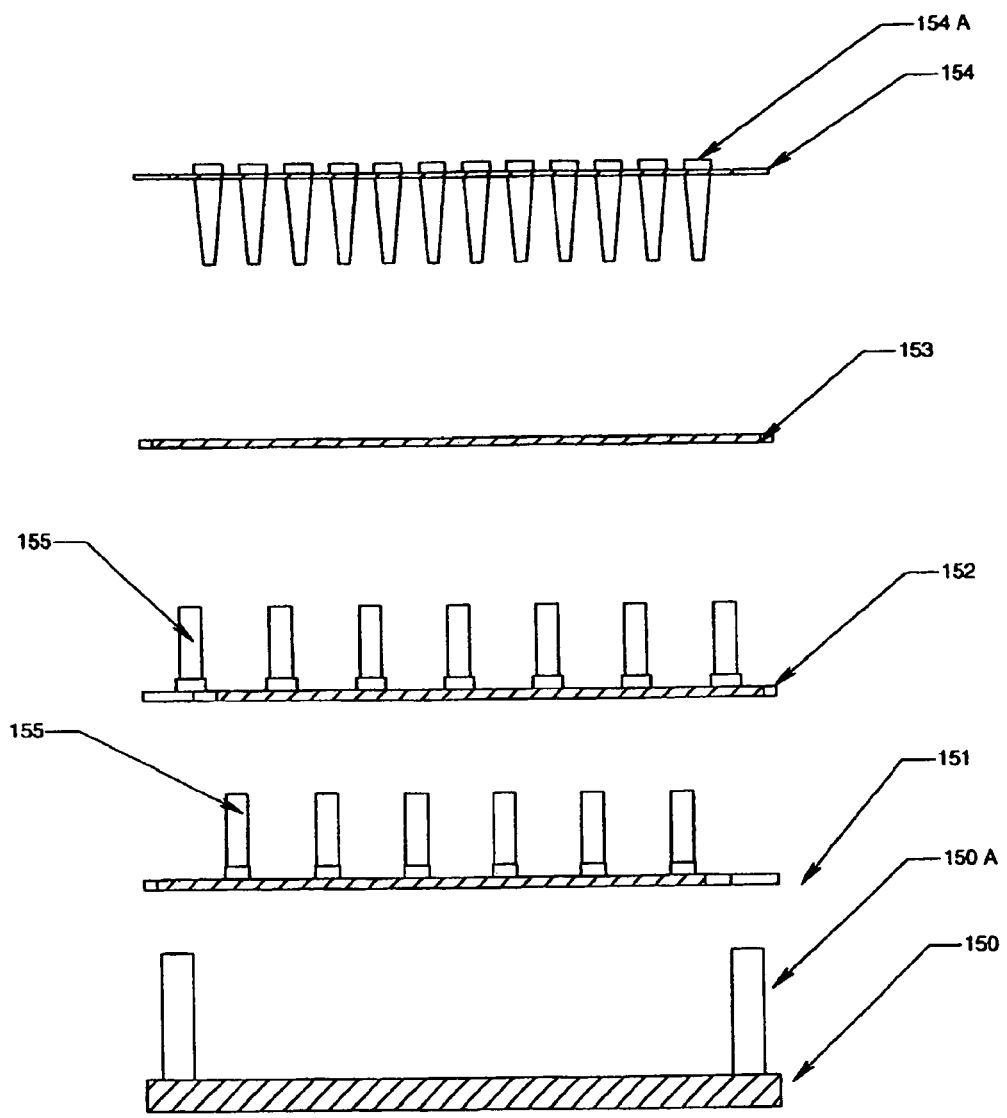
Figure 15:
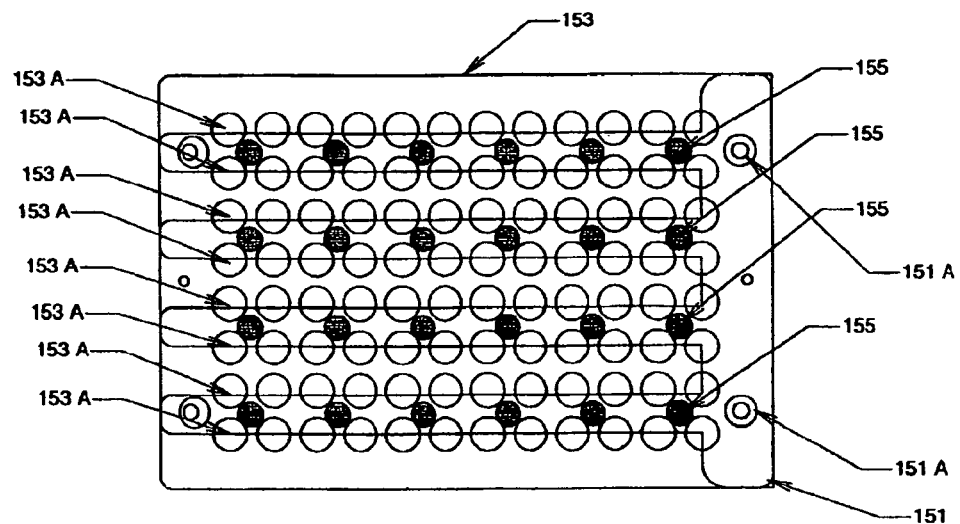
Figure 15:
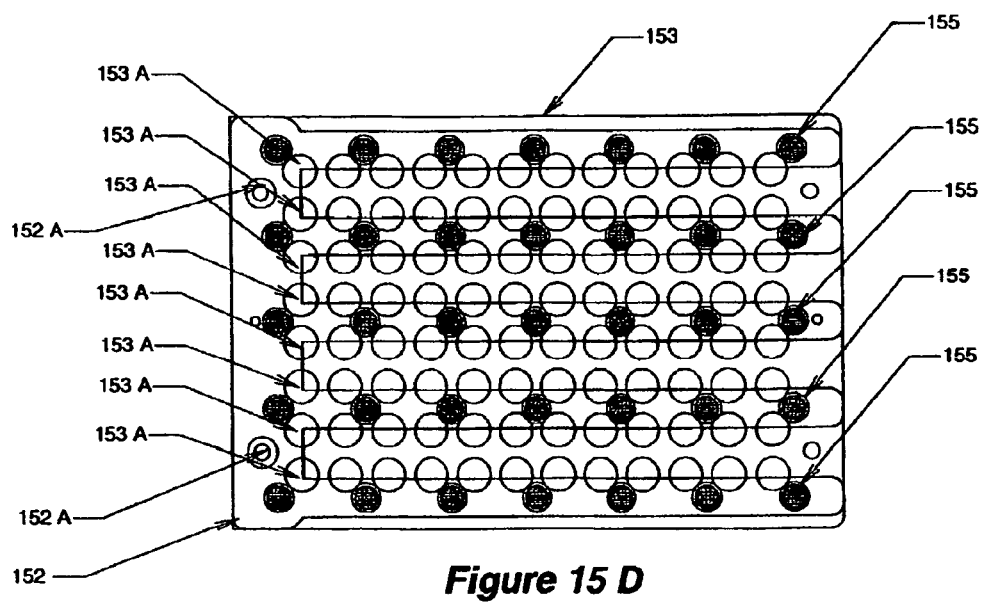

FIG. 13-15 shows other preferred embodiments of the present invention which generally include a "sample plate" with apertures for holding the containers, and a "magnet plate" with at least two arrays of magnets mounted onto it, and a "base plate" with at least 2 "side plates" supporting the "sample plate" and "magnet plate".

The magnet arrays in either a circular or rectangular pattern are mounted on the "magnet plate". The change in the relative angular position between the magnetic particles in the liquid sample in a container is preferably effected in a single step movement at a suitable acceleration by an electric step motor. Either the sample plate or the magnet plate can be moved and such motion linear or rotary so that each successive movement brings the opposite lateral sides of the container in front of the staggered magnets. Such an angular change between the container and magnet brings about the re-suspension and mixing of the magnetic particles in the liquid sample in a manner analogous to the 180° step rotation movement described earlier. In the absence of such movement, the magnetic particles in the liquid sample move to lateral side inside the container nearest to the magnet and thus separated from the liquid sample.

The devices according to the invention are advantageous for processing large number of samples and of great utility in molecular diagnostics, forensic DNA analysis and molecular biology fields.

FIG. 13 A-C shows various isometric views of a device with the four side plates covering the device removed. It includes a base plate 131, an electric motor 137, preferably a step motor, a chuck 136 mounted on the motor shaft 137 A, a magnet plate 132 with plurality of magnets 134 mounted in a circular pattern, a round shape sample plate 133 with alias plurality of apertures for inserting containers 135 with the magnetic particles in a liquid sample. Hereafter container shall mean container with a suitable volume of a liquid sample containing magnetic particles. Disposable plastic test tubes such as Eppendorf type of tubes are preferred but other types can also be used.

Sample plate 131 includes 2 holes 133 B, which tightly fits into the aligning dowels 136 B on the chuck 135 to align the four holes 133 C with the four threaded holes 136 A of the chuck through which four threaded screws are used to fasten sample plate 131 to chuck 136. Sample plate can be rotated by motor 137, preferably at predetermined angular positions in successive steps preferably with a delay time between each step. The electric motor will be driven by appropriate electronic motion controllers, available through many vendors such as Nyden Company, Fremont, Calif.

The magnet plate 132 is attached to the top frame of motor 137 through four holes 135 by long fasteners screwed to the base plate 131 so that both the motor 137 and magnet plate 132 remain firmly secured. The magnet plate 132 has a plurality of magnets 134 mounted in two circular arrays, which are concentric. The circular magnet arrays are sufficiently spaced apart to allow the free rotation of the containers 135 between them.

Permanent magnets of rectangular shape are preferred but other shapes such as cylindrical can also be used. High-energy magnets of the NdFeB type are particularly preferred. The magnets 134 will be of appropriate size (width and length) to provide sufficient magnetic field strength over substantial part of the lateral surface area of the container 135. The arrangement where similar poles such as north-north or south south are diametrically opposite one another relative to the container is preferred. As shown in FIG. 13 B, the individual magnets 134 in the two circular arrays are positioned diametrically opposite one another relative to the container but staggered so that the magnetic field inside the container generated by one magnet is substantially unaffected by the magnetic field generated by the other magnet.

For example, in a device for Eppendorf type of container, the magnets of the size about 10×10×25.4 mm was used in two circular arrays. When assembled (FIG. 13 A), the distance between the magnet plate 132 and the sample plate was adjusted to about 11-17 mm distance so that the container rotates without hindrance.

Sample plate 133 was rotated by the step motor 137 in steps of about 30°, which positions the container in successive steps in front of the magnets, which are diametrically opposite side of the container. This brings about an 180° change in the direction of magnetic field attracting magnetic particles in the liquid sample. Continuing this step-wise rotation suspended and mixed the magnetic particles. On stopping the rotation, the container remained stationary in front of the magnet resulting in the separation of the magnetic particles from the liquid sample. A 15° step move brought the container at an intermediate position between the magnets to substantially remove the effect of magnetic field on the container which was useful in some downstream application such as eluting the affinity bound nucleic acids from the magnetic particles.

Although rotary motion of the sample plate has been described, it is obvious that the sample plate can be fixed while the magnet plate is rotated and such a configuration may useful in certain situations.

FIG. 14 A-D shows various isometric views of a device with a linear array magnet mounted in assemblies arranged in of plurality of rows over the magnet plate and parallel over it a sample plate with plurality of apertures for holding the containers.

It includes a base plate 141 with two parallel side plates 142 A-B with rectangular grooves 142 G mounted thereon, a magnet plate 143 with nine magnet assembles mounted in equidistance rows with assembly 146 A alternating with respect assembly 146 B and a sample plate 144 fixed over the top of side plates 142 A-B and a sample plate 144 mounted over the side plates 142 A-B and has an 8×12 array of apertures 144 A for inserting the containers 145 containing magnetic particles in liquid samples. As shown in FIG. 14 B, the left and right sides of magnet plate 143 can be inserted in the groove 142 G of the two parallel side plates 142 A-B to provide a guided linear sliding movement of the magnet plate parallel to the sample plate 144. The magnet plate 143 can be mechanically attached to a linear electric step motor, linear actuator or other suitable motorized mechanical means to horizontally move the magnet plate within the linear guide of the two grooves 142 G.

The magnet assemblies 146 A-B comprises of magnets 147 fixed in evenly spaced slots of a non-magnetic harness by an adhesive or suitable mechanical means with seven magnets in 146 A and six magnets in 146 B. Permanent magnets are preferred, particularly high energy magnets of NdFeB type. The magnets 147 will be of appropriate size (width and length) to provide sufficient magnetic field strength over substantial part of the surface area of the container 146. The arrangement where similar poles are diametrically opposite one another relative to the container is preferred.

As shown in FIG. 14 C, the magnet plate 143 has a plurality of magnet assemblies mounted equally spaced and parallel rows with magnet assembly 146 A alternating magnet assembly 146 B. The separation distance between the assemblies should be sufficient to allow a hindrance free movement of magnet assemblies 146 A-B with respect to the containers 145 between them.

FIG. 14 D is a partial cut of the top view of the invention showing the apertures 133A of the sample plate are positioned at the center between magnet assemblies 146 A-B. It will be recalled that the containers 145 containing magnetic particles in a liquid sample would be inserted through the apertures 133 A in the sample plate. The positions of the containers will therefore be identical to the positions of apertures. Referring to FIG. 14 D, it can be seen that individual containers in each row are precisely positioned in front of the alternating individual magnets 147 in the magnet assembly 146 A and magnet assembly 146 B. The direction of the magnetic field acting on the lateral side of the containers alternately reverses. It should be noted that magnetic field generated by one magnet is substantially unaffected by the magnetic field generated by the other magnet.

When magnet plate 143 is stationary with magnets and the sample containers in their respective arrays aligned, magnetic particles inside the containers will collect on the lateral wall of the containers nearest to its respective magnets. A linear step movement of the magnet plate 143 will position the magnets at the diametrically opposite side of the containers thereby attracting the magnetic particles to a position opposite to previous. Repeated forward and backward step-wise motion of the magnet plate will cause the suspension and mixing of magnetic particles in the liquid sample and when this motion is stopped separation of magnetic particles.

The invention shown in FIG. 14 A, can process 96 Eppendorf types of containers simultaneously. It contains the permanent magnets of about 10×10×25.4 mm size which are mounted in the evenly spaced of about 50.8 mm slots in the magnet assembly with seven magnets in magnet assembly 146 A and six magnets in 146 B. Nine rows of magnet assemblies were mounted on the magnet plate 143 with five of assembly 146 A alternating with four of assembly 146 B. A distance of about 12 mm separated the rows of assemblies. When assembled, the distance between the magnet plate 143 and the sample plate 144 is adjusted to so that Eppendorf sample container 145 is maximally exposed to the magnets 143 and the magnet plate 143 moves without hindrance.

The magnet plate was mechanically connected to a linear step motor to horizontally move the magnet plate 143 to about 25.4 mm lateral distance mm in the forward and backward directions. A delay time of about 0.5 to 60 seconds was imposed during each stroke of the linear movement. Such a motion profile was electronically controlled and repeatedly positioned the magnets at the diametrically opposite side of the container which suspended and mixed the magnetic panicles inside the Eppendorf until the motor was stopped to separate the magnetic particles from the liquid samples.

Although linear motion of the magnet plate is described, it is obvious that the magnet plate can be fixed while the sample plate is horizontally moved to repeatedly position the sample container between the diametrically opposed magnets.

FIG. 15 shows an isometric view of an apparatus for mixing and separating magnetic particles in the wells of a 96-well microplate. FIG. 15 A is an exploded isometric view corresponding to FIG. 15 and shows a base plate 150 with four guide rods 150 A, two magnet assemblies 151-152 with magnets 155 mounted in linear arrays thereon, a sample plate 153 with apertures for inserting the 96 wells 154A of the microplate 154.

The disposable plastic microplates 154 known as "skirt-less" type are widely available and have integrally formed multiple wells for holding liquid samples. As shown in FIG. 15 A, the wells 154 A in the microplate 154 are closely spaced and arranged in an 8 by 12 array. The volumetric capacity of the wells is usually in time range of 250-350 micro liters. While a ninety-six well microplate is shown, this invention is equally applicable to standard 6, 12, 24, 48 tissue culture plates as well as 96-well microplates with a volumetric capacity of 1-2 ml.

The magnet 155 are preferably of cylindrical shape and the high energy magnets of NdFeB type in order to provide strong magnetic fields adjacent to wells in microplate 154.

The magnet assemblies 151 and 152 are slotted in the shape of "fingers" in order to permit the unhindered independent movement of either magnet assembly in the vertical direction to place the magnets between the wells of microplate. A rectangular plate with appropriate access holes for magnet passage can also be used instead of the slotted shape for magnet assemblies.

The magnet assembly 151 includes guide holes 151A and a 4×6 array of individual rod-shaped magnets mounted on the four slots of the assembly. The magnet assembly 151 is precisely positioned by inserting it through the guide holes 151 A in the two individual guide rods 150A mounted on the right of the base plate 150. The magnet assembly 152 include two guide holes 152A and a 5×7 array of individual rad-shaped magnets mounted on the five slots of the assembly. The magnet assembly 152 is similarly positioned by inserting it through the guide holes 152 A in the two individual guide rods 150 A mounted on left of the base plate 150. Both magnet assembles can be independently moved up towards the bottom of microplate 154 through the linear guide provide by the holes and rods. A suitable roller bearing may be used in the holes to provide a rigid mechanical support to assemblies as well as friction less movement. Each assembly can be mechanically attached to a linear electric step motor, linear actuator or other suitable motorized mechanical means to provide independent movement to each assembly. FIG. 15 B shows a front view corresponding to FIG. 15 A, illustrating the relative positions of the mounted magnets 155 in the assemblies with respect to wells micro plate. The gaps between slots of the assembly 152 (hidden) allow the positioning of mounted magnets of the assembly 151 between the well of the micro plate 154.

The sample plate 153 has a plurality of apertures 154 A arranged as 8×12 array of individual apertures corresponding to 8×12 array of individual wells of the microplate through which the wells can be inserted and precisely positioned with respect to magnets 155 mounted on the two magnet assemblies 151 and 152. The sample plate 153 is fixed at the top of four guide rods 150 A by means of threaded fasteners. The micro plate thus remains fixed and the wells precisely positioned to permit access of mounted magnets between the exterior spaces of the wells underneath the microplate 154. Sufficient distance between the base plate 150 and the sample plate so that magnetic field of the mounted magnets 155 acting on the wells of micro plate is negligible. Magnetic field becomes active only when the magnet assembly is moved upward and the mounted magnets positioned between the wells of the micro plate 154 and near the sample plate surface underneath.

FIG. 15 C shows the relative positions of the 4×6 array of magnets and the 8×12 array of apertures 153 A when the magnet assembly 151 upward near the sample plate 153. Apertures can be assumed to represent the wells, as the 8×12 array patterns of both the sample plate 153 and micro plate 154 are identical. Referring to FIG. 15 C it can be seen that the 24 magnets are uniformly distributed within the boundaries of 96 wells and the radial magnetic field of each individual magnet essentially acts on four surrounding wells. Magnet positions in each row aid column are sufficiently apart so that the effect of their magnetic fields on the distant wells can be considered negligible. Magnetic particles in the liquid sample in each set of four wells will move and aggregate on the lateral surfaces inside the wells nearest to the magnets.

FIG. 15 D shows the relative positions of the 5×7 array of magnets and the 8×12 array of apertures 153 A when the magnet assembly 151 is moved down and the magnet assembly 152 is moved upward near the sample plate 153. As previously, the apertures can be assumed to represent the wells.

A comparison between FIGS. 15 C and D Figure, reveals that the magnets in the magnet assemblies 151 and 152 are positioned diametrically opposite one another relative to the wells of microplate 154 and the radial magnetic field of each individual magnet will now attract the magnetic particles in the liquid sample in each well on the diametrically opposite lateral surface inside each well.

Successive rapid upward movement of one magnet assembly at a time while the other magnetic assembly is rapidly moved down will bring about the mixing of magnetic particles in the liquid sample in each well in a similar manner as described earlier. For the separation of magnetic particles in the wells either one or both magnetic assemblies may be moved upward and made stationary till all the particles have separated in the wells, which permits the removal of the supernatant liquid.

Figure 16:
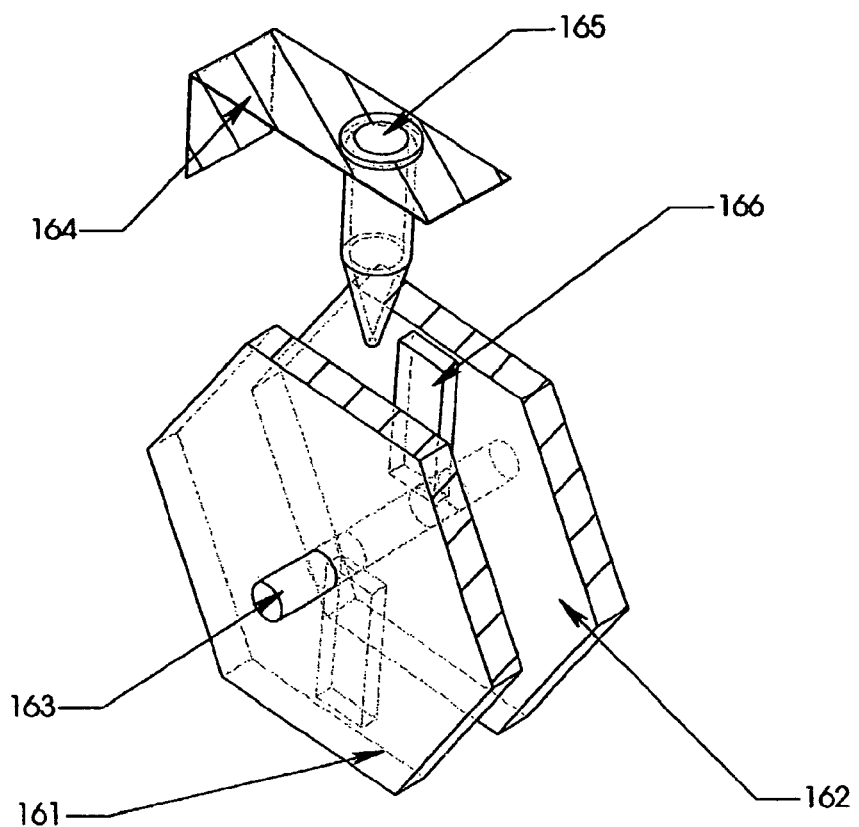
FIG. 16 A shows an isometric view of yet another preferred embodiment of the invention, which includes a container, mounted in a fixed holder and positioned between two concentric rotor discs fixed to a rotating shaft.
Figure 16:
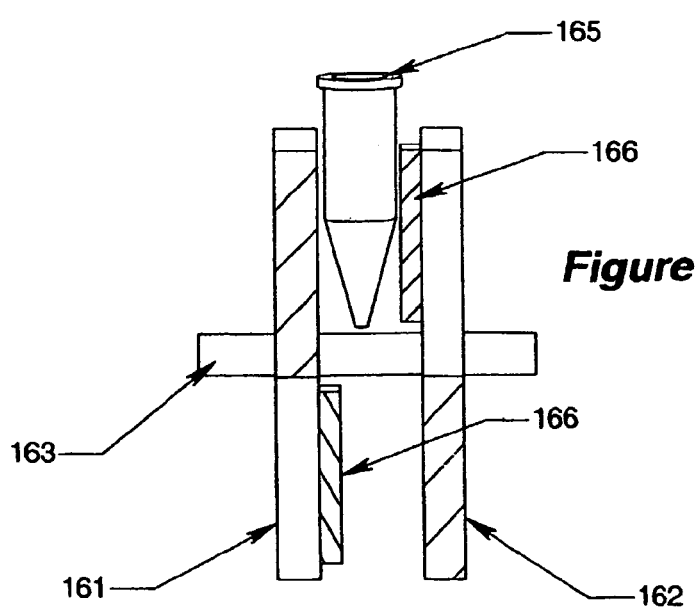

FIG. 16 A shows an isometric view of a device for single container preferably a container of large volumetric capacity such as 50 ml. It includes a magnet assembly comprised of two hexagonal magnet plates 161 and 162, each with a mounted magnet 166. Rare earth high-energy magnets are preferable and appropriate dimensions to provide maximum magnetic field area to cover the lateral part of the container 165. Both the magnet plates are fixed to the shaft 163 in parallel coaxial positions with the two magnets opposite each other and separated by an angular position of 90° and preferably by an angle of 180°. Other angular positions may be used provided that magnetic field generated by one magnet is substantially unaffected by the magnetic field generated by the other magnet. Although rectangular magnets are preferred, round or other suitable shapes for magnets can also be used. Similarly, shapes other than hexagonal can also be used for magnet plates.

The shaft 163 can be the shaft of a step motor to directly rotate the magnet plates or a separate cylindrical shape rod, which can be reversibly attached to a step motor shaft with a suitable shaft coupler such as Fairloc Shaft Coupling available from Stock Drive Products, N.Y.

The sample plate 166 includes an aperture for inserting the container 165 and is attached to a height adjustable clamp of a laboratory stand to permits the positioning of the container 165 at the center of the two magnet plates without hindering its rotary movement of the magnet plates as shown in FIG. 16 B. When the shaft is rotated, the two coaxial magnet plates rotate simultaneously which successively brings each mounted magnet at the opposite lateral sides of the container. Step motion of a predetermined angle by step motor with an imposed delay time of about 0.5 second between each step is preferred to suspend and mix the magnetic panicles in the sample liquid of the container and by stopping this rotation and positioning one of the magnet adjacent to the container separates magnetic particles from the liquid sample on the lateral wall inside the container to allow the removal of the supernatant liquid.

The relative angular movement is induced in the magnetic particles by either rotating a magnetic field around a stationary container or rotating the container relative to an immobile magnetic field. The magnet creating the field is disposed outside the container and defines a cavity of magnetic field gradient within the liquid test medium. Any container configuration may be utilized, such as, for example, a doughnut-shaped container. In such a container the magnetic source may be "outside" of the container and "within" the container, if it occupies the hole of the doughnut. Therefore, it is to be understood that, within the scope of the appended claims, the invention may be practiced otherwise than as specifically described herein.

The following examples further describe in detail the manner and process of using the present invention. The examples are to be considered as illustrative but not as limiting of this invention. All manipulations given in the examples are at ambient temperature unless otherwise indicated.

EXAMPLE 1

The effect of angular acceleration on magnetic particle mixing was determined by using a device similar to the apparatus shown in FIG. 12 except that the linear drive mechanism for vertical movement of the magnet assembly was switched off. The magnet assembly included six rare earth type (Nd-FeB) permanent magnets of about 35 MGOe. The electric motor (FIG. 12, 129) was a two phase stepping motor driven by a computer programmable controller-driver. The rotary motion of the stepper motor responds to sequence of digital pulses from the controller-driver. The angular acceleration is directly related to the frequency of input pulses and the length of rotation is directly related to number of pulses applied. A 1.6 ml microcentrifuge tube having diameter of about 10.6 mm was used as a container. A 250 µl suspension of about 50 million paramagnetic beads in phosphate buffer saline, pH 7.5 containing 2.5% bovine serum albumin was transferred to a microcentrifuge tube. The beads were obtained from Dynal, Inc., and their reported physical characteristics were: spherical and uniform size of 4.5 µm, magnetic mass susceptibility of about 16×10-5 m3/kg. The microcentrifuge tube was placed in the holder (FIG. 12, 134) and the magnetic field acting inside of the microcentrifuge tube was adjusted by the knob (FIG. 12, 128) so that the suspended beads aggregate within 60 seconds at the inside wall closest to the magnet assembly. The magnetic field gradient measured inside the container varied from about 1.1 kGuass (closest to magnet) to about 0.4 kGuass (farthest from magnet). Once the magnetic beads had aggregated, the microcentrifuge tube was accelerated from rest to a preselected speed (rpm) within one second time. The angular acceleration was calculated from the following formula:

$$\alpha = (\omega_1 - \omega_0)/t = \text{rad/s}^2$$

Where α angular acceleration (rad/s$^2$), $\omega_1$ is angular velocity in radians per second after one second, ω0 angular velocity in radians per second at rest which in this instance is zero, and t is the time in second which in this instance is one second. The mixing efficiency of the beads at various acceleration rate was estimated by observing the mass of beads remaining aggregated as well as the cloudiness of the suspension (scale of + to 5+). Continuous rotation was used for speeds between 5 to 200 rpm. The effect of acceleration on mixing efficiency could be clearly observed when tube was accelerated from rest to an angular position of 180° in a single step and stopped. Although a microscope may be used but a visual examination was also adequate. The results are shown in Table 1.

TABLE 1

| Speed (rpm) | $\omega_1$ (rads/s) | $\alpha$ (rads/s$^2$) | Mixing Efficiency |
|---|---|---|---|
| 5 | 0.52 | 0.10 | No Mixing, beads remain substantially aggregated |
| 10 | 1.05 | 0.21 | No Mixing, beads remain substantially aggregated |
| 40 | 4.19 | 0.84 | Cloudiness +, about 90% beads remain aggregated |
| 50 | 5.24 | 1.05 | Cloudiness ++, about 80% beads remain aggregated |
| 100 | 10.47 | 2.09 | Cloudiness +++, about 30% beads remain aggregated |
| 200 | 20.94 | 4.19 | Cloudiness +++++, less than 5% beads remain aggregated |
| 180° Step | 209.44 | 41.89 | 100% mixing |

EXAMPLE 2

The effect of angular acceleration on purification efficiency was determined by isolating genomic DNA from human whole blood. The basic experimental set up was as described in Example 1 and angular acceleration of 0.1, 0.21 and 4.19 rads/s2 was used. The experiments consisted of three identical isolations using EDTA anticoagulated blood and magnetic beads from Dynabeads DNA Direct kit (commercially available from Dynal, Inc., Lake Success, N.Y. 11042). The process of DNA isolation in this kit relies upon cell lysis to release the DNA, which is then adsorbed at the surface of the beads. It was assumed that mixing efficiency would be directly reflected by comparing the yields of DNA isolated at the three angular acceleration. A 200 µl suspension of beads from the kit was pipetted in a siliconized microcentrifuge tube. The microcentrifuge tube was then placed in the tube holder of the apparatus and the magnetic field acting inside of the tube was adjusted by the knob (FIG. 12, 128) so that the suspended beads aggregate within 60 seconds at the inside wall closest to the magnet assembly. Once the beads had aggregated, a 10 µl of EDTA anticoagulated blood was added to the clear solution inside the tube. The microcentrifuge tube was accelerated from rest to a preselected speed (rpm) and the rotation of the tube was continued for about five minutes. During this rotation, the beads, if mixing, would adsorb DNA. The rotation was then stopped and the magnetic field acting inside of the tube was increased to maximum by bringing the magnet assembly closest to the tube holder by adjusting the knob (FIG. 12, 128). The beads aggregated at the inside wall closest to the magnet assembly and the supernatant was withdrawn. The beads were then washed twice with 200 µl of the wash buffer of the kit. During each washing the beads were mixed in the washing buffer by rotating the tube for two minutes at the angular acceleration used for DNA adsorption. The steps for the separation of beads and removal of supernatant wash buffer were as described earlier. The tube was then removed from the apparatus and bead/DNA complex resuspended in 50 µl of resuspension buffer of the kit (10 mM Tris HCl, pH 8.0) by pipetting up and down 30-40 times until the suspension is homogenous. DNA was then eluted by incubating the tube at 65 Co for five minutes. The tube was then placed back on the apparatus to separate the beads and the supernatant containing the eluted DNA was transferred to a dean tube. The DNA content in the supernatant was then determined by measuring optical density (OD) at 260 and 280 nm. The ratio $OD_{260}/OD_{280}$ of 1.7 indicated that the isolated DNA was pure. The OD260 was then used to calculate the concentration of DNA. This technique for the determination of DNA is well known and widely used in the molecular biology art. The yields of genomic DNA isolated at angular acceleration of 0.1, 0.21 and 4.19 rads/s2 are shown in Table 2.

TABLE 2

| Speed (rpm) | $\alpha$ (rads/s$^2$) | Mixing Efficiency | DNA Yield ng |
|---|---|---|---|
| 5 | 0.10 | Aggregated beads roll over one another | Un-detectable |
| 10 | 0.21 | Aggregated beads roll over one another | Un-detectable |
| 200 | 4.19 | Beads are dispersed and mixed | 250 |

What is claimed is:

1. A method of causing a biospecific binding reaction between a solid phase and a liquid phase, the method comprising:
   placing the liquid phase into a magnetically permeable container having a cylindrical shape with a vertical axis, the liquid phase comprising a first member of a biospecific affinity binding pair;
   placing the solid phase inside the magnetically permeable container, the solid phase comprising magnetic particles coated with a second member of the biospecific affinity binding pair;
   generating a magnetic field gradient inside the magnetically permeable container along a second axis perpendicular to the vertical axis using at least one magnet, the magnet or magnetically permeable container being movable relative to the other;
   moving at least a portion of the magnetically permeable container or the magnet relative to the other along the second axis to change the relative angular position of the magnetic particles with respect to the magnet;
   moving the magnet or magnetically permeable container along the vertical axis relative to the other concurrently with the step of moving at least a portion of the magnet or the magnetically permeable container along the second axis; and
   causing a biospecific affinity binding reaction between the first member of the biospecific affinity binding pair and the second member of the biospecific affinity binding pair.

2. The method of claim 1, comprising forming at least one chain of magnetic particles and breaking the chain of magnetic particles to form a cloud of magnetic particles within the magnetically permeable container.

3. The method of claim 1, wherein moving the magnetically permeable container or magnet relative to the other along the second axis comprises rotating the magnet or magnetically permeable container relative to the other.

4. The method of claim 1, wherein the first member of the biospecific affinity binding pair comprises a target cell population.

5. The method of claim 1, wherein the first member of the biospecific affinity binding pair comprises stem cells.

6. The method of claim 1, wherein causing a biospecific affinity binding reaction comprises carrying out an immunospecific cell separation.

7. A method of isolating a cell population from a fluid by using a biospecific affinity binding reaction, the method comprising:
- placing a fluid volume into a magnetically permeable container having a cylindrical shape with a vertical central axis;
- placing magnetic particles inside the magnetically permeable container, the magnetic particles comprising one member of a specific affinity binding pair capable of binding one or more cells from the cell population;
- generating a magnetic field gradient inside the magnetically permeable container along a second axis perpendicular to the vertical central axis using at least one magnet, the magnet or magnetically permeable container being movable relative to the other;
- rotating the magnetically permeable container about an axis of rotation parallel to the vertical central axis;
- moving the magnet or magnetically permeable container parallel to the vertical central axis concurrently with the step of rotating the magnetically permeable container; and
- binding the cell population of the fluid volume to the magnetic particles.

8. The method of claim 7, comprising forming at least one chain of magnetic particles and breaking the chain of magnetic particles to form a cloud of magnetic particles within the magnetically permeable container.

9. The method of claim 7, wherein the specific affinity binding pair comprises stem cells.

10. A mixing apparatus for use with magnetic particles, the apparatus comprising:
- a first container having a first cylindrical wall with a first diameter and defining a first volume, the first container configured to receive a mixture of a first set of magnetic particles, first target cells, and a first fluid;
- a second container having a second cylindrical wall with a second diameter and defining a second volume, the second container configured to receive a mixture of a second set of magnetic particles, second target cells, and a second fluid;
- an apparatus housing;
- a first holder configured to releasably connect to the apparatus housing, the first holder configured to receive at least a portion of the first container and to rotate the first container about a first axis of rotation;
- a second holder configured to releasably connect to the apparatus housing, the second holder configured to receive at least a portion of the second container and to rotate the second container about a second axis of rotation parallel to the first axis of rotation;
- a first magnet movable in a direction parallel to the first axis of rotation; and
- a second magnet movable in a direction parallel to the second axis of rotation.

11. The mixing apparatus of claim 10, wherein the first diameter is greater than the second diameter.

12. The mixing apparatus of claim 10, wherein the first magnet moves parallel to the first axis of rotation simultaneously as the first holder rotates the first container about the first axis of rotation.

13. A method of binding cells to magnetic particles, the method comprising:
- positioning a first container in a first holder, the first container having a first diameter;
- positioning a second container in a second holder, the second container having a second diameter;
- rotating the first container about a first axis of rotation;
- rotating the second container about a second axis of rotation parallel to the first axis of rotation;
- moving a first magnet in a direction parallel to the first axis of rotation with respect to the first container;
- moving a second magnet in a direction parallel to the second axis of rotation with respect to the second container;
- interchanging the first holder with a third holder; and
- positioning a third container in the third holder, the third container having a third diameter different from at least one of the first diameter and the second diameter.

14. The method of claim 13, comprising transferring a first set of magnetic particles, a first set of target cells, and a first fluid into the first container and transferring a second set of magnetic particles, a second set of target cells, and a second fluid into the second container.

15. The method of claim 14, wherein the first set of target cells comprise cells that are different from cells in the second set of target cells.

16. The method of claim 14, wherein the first set of target cells include stem cells.

17. The method of claim 13, wherein the rotating the first container is performed contemporaneously with moving the first magnet in a direction parallel to the first axis of rotation.

* * * * *